| (12) United States Patent<br>Burkett | (10) Patent No.: US 10,251,569 B2<br>(45) Date of Patent: Apr. 9, 2019 |

(54) CONNECTION STRUCTURES FOR INTRAVASCULAR DEVICES AND ASSOCIATED SYSTEMS AND METHODS

(71) Applicant: VOLCANO CORPORATION, San Diego, CA (US)

(72) Inventor: David Burkett, Panama City Beach, FL (US)

(73) Assignee: VOLCANO CORPORATION, San Diego, CA (US)

( * ) Notice: Subject to any disclaimer, the term of this patent is extended or adjusted under 35 U.S.C. 154(b) by 0 days.

(21) Appl. No.: 15/694,947

(22) Filed: Sep. 4, 2017

(65) Prior Publication Data

US 2018/0008153 A1 Jan. 11, 2018

Related U.S. Application Data

(63) Continuation of application No. 13/930,692, filed on Jun. 28, 2013, now Pat. No. 9,750,417.
(Continued)

(51) Int. Cl.
*A61B 5/00* (2006.01)
*A61B 8/00* (2006.01)
(Continued)

(52) U.S. Cl.
CPC .......... *A61B 5/0215* (2013.01); *A61B 5/6852* (2013.01); *A61B 8/12* (2013.01);
(Continued)

(58) Field of Classification Search
CPC ......... A61B 5/2015; A61B 8/12; A61B 8/445; A61M 25/09
See application file for complete search history.

(56) References Cited

U.S. PATENT DOCUMENTS

| 3,289,149 A | 11/1966 | Pawloski |
| 5,016,646 A * | 5/1991 | Gotthardt ............... A61N 1/056 607/122 |
| 6,078,831 A | 6/2000 | Belef et al. |
| RE44,667 E | 12/2013 | Rock |

(Continued)

FOREIGN PATENT DOCUMENTS

| EP | 1803481 A2 | 7/2007 |
| WO | 1995017131 A1 | 6/1995 |
| WO | 1999016347 A1 | 4/1999 |

OTHER PUBLICATIONS

European Searching Authority—Berlin/European Patent Office, "Supplementary Search Report", for European Application No. 13810289.2, dated Mar. 7, 2016, 8 pages.
International Searching Authority/United States Patent Office, "Notification of Transmittal of the International Search Report and the Written Opinion of the International Searching Authority, or the Declaration", for PCT/US2013/048539 dated Oct. 11, 2013, 12 pages.

*Primary Examiner* — Sean P Dougherty

(57) ABSTRACT

Intravascular devices, systems, and methods are disclosed. In some embodiments, a method of assembling an intravascular device is provided that includes positioning a first tubular member around a plurality of conductors and a core member; advancing a first of the plurality of conductors through an opening of the first tubular member; positioning a first conductive member around the first tubular member; and electrically coupling the first of the plurality of conductors to the first conductive member. In some embodiments, an intravascular device is provided that includes an insulating member positioned around a plurality of conductors and a core member and a conductive member positioned around the insulating member, wherein at least one of the plurality of conductors extends through an opening in the insulating (Continued)

member and is electrically coupled to the first conductive member.

14 Claims, 14 Drawing Sheets

Related U.S. Application Data

(60) Provisional application No. 61/665,739, filed on Jun. 28, 2012.

(51) Int. Cl.
*A61B 8/12* (2006.01)
*A61M 25/09* (2006.01)
*A61B 5/0215* (2006.01)

(52) U.S. Cl.
CPC ........... *A61M 25/09* (2013.01); *A61B 5/0084* (2013.01); *A61B 8/445* (2013.01); *A61B 8/56* (2013.01); *A61B 2562/12* (2013.01); *Y10T 29/49208* (2015.01)

(56) References Cited

U.S. PATENT DOCUMENTS

| | | |
|---|---|---|
| 8,600,518 B2 | 12/2013 | Meadows et al. |
| 2003/0088193 A1 | 5/2003 | Malmborg et al. |
| 2004/0181177 A1 | 9/2004 | Lee et al. |
| 2004/0267115 A1 | 12/2004 | Carr |
| 2007/0168004 A1 | 7/2007 | Walter |
| 2009/0079519 A1 | 3/2009 | Iyer |
| 2010/0262040 A1 | 10/2010 | Von Malmborg |
| 2011/0046494 A1 | 2/2011 | Balji et al. |

\* cited by examiner

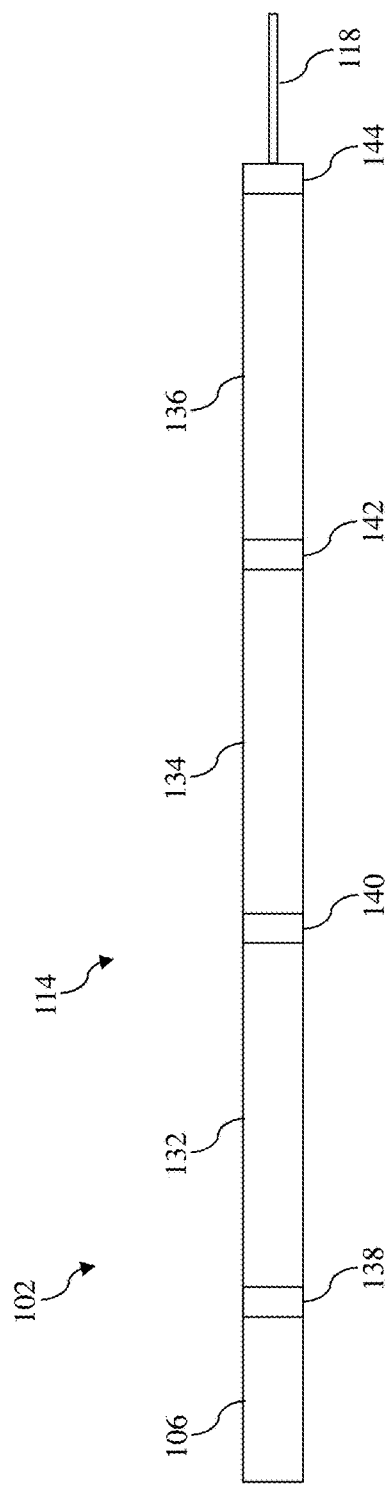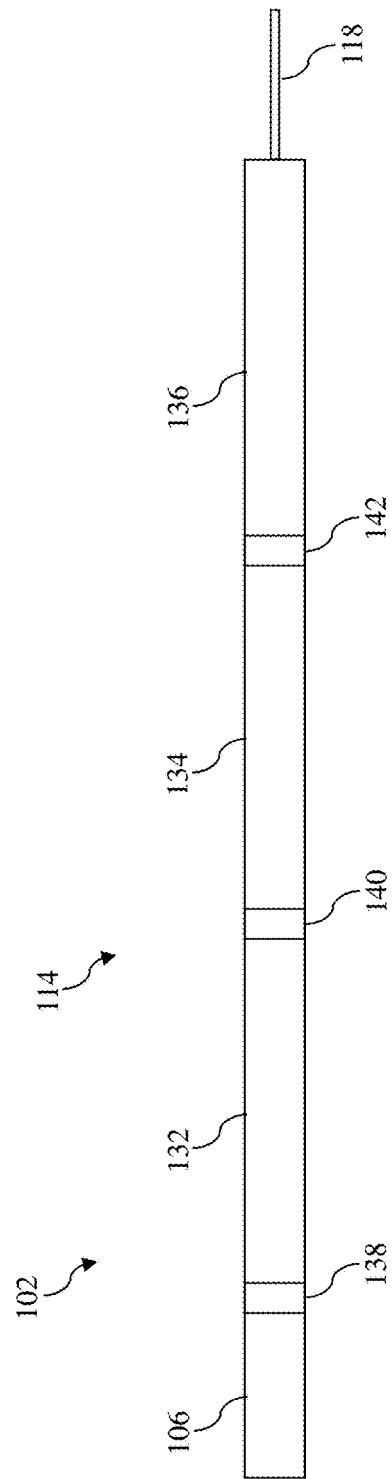

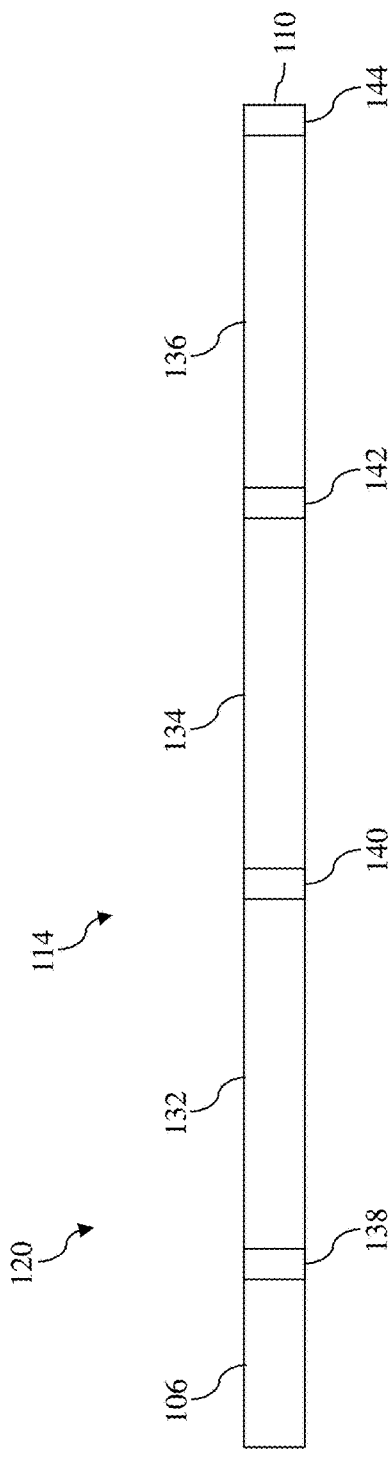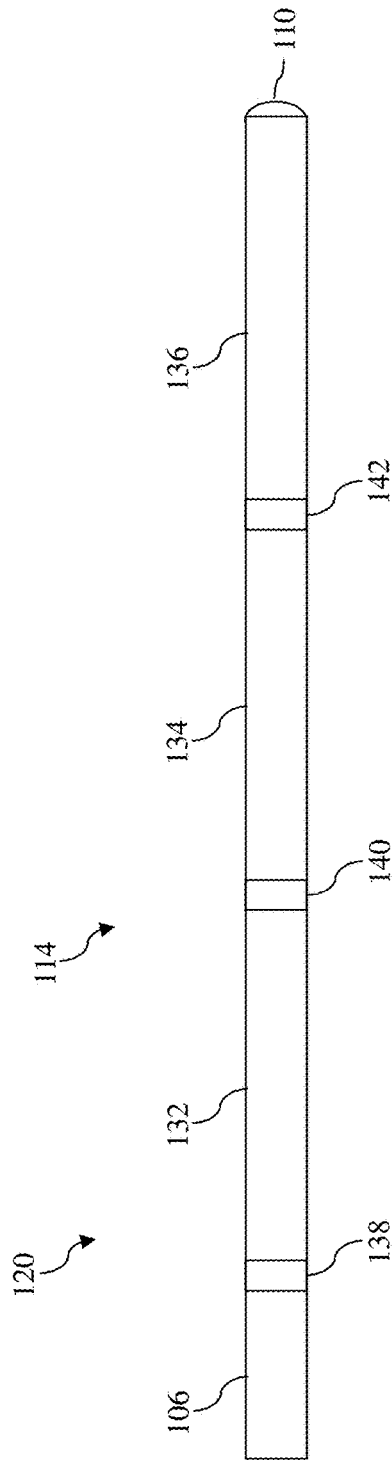

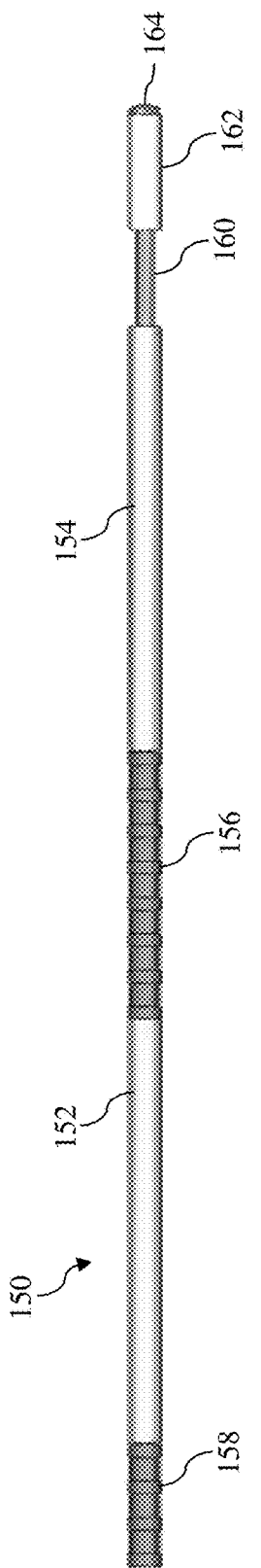
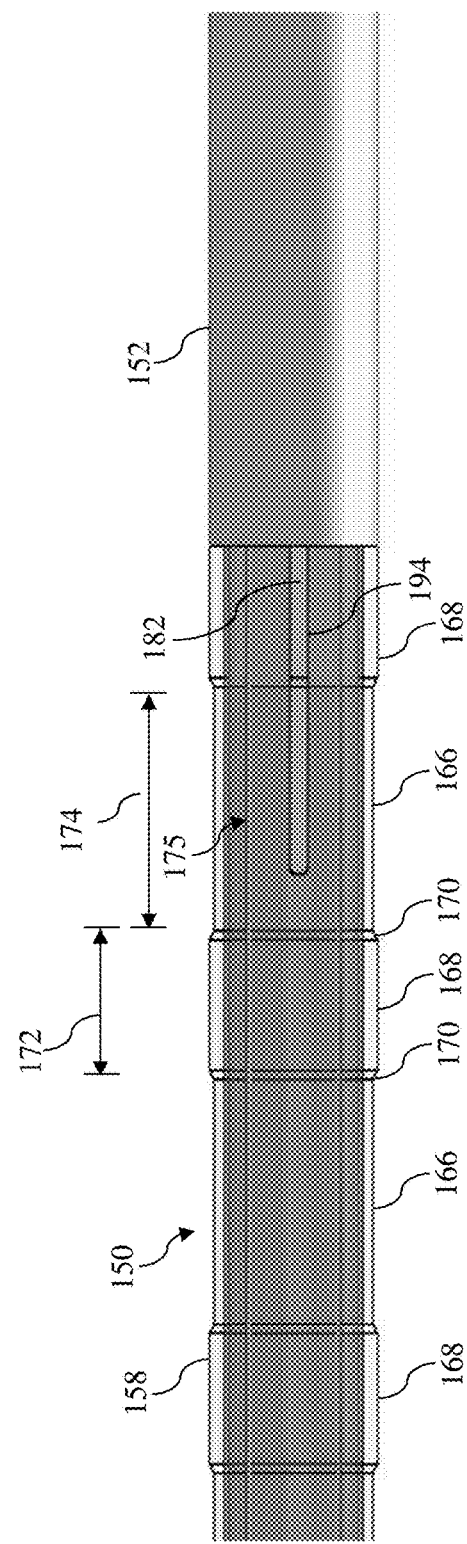

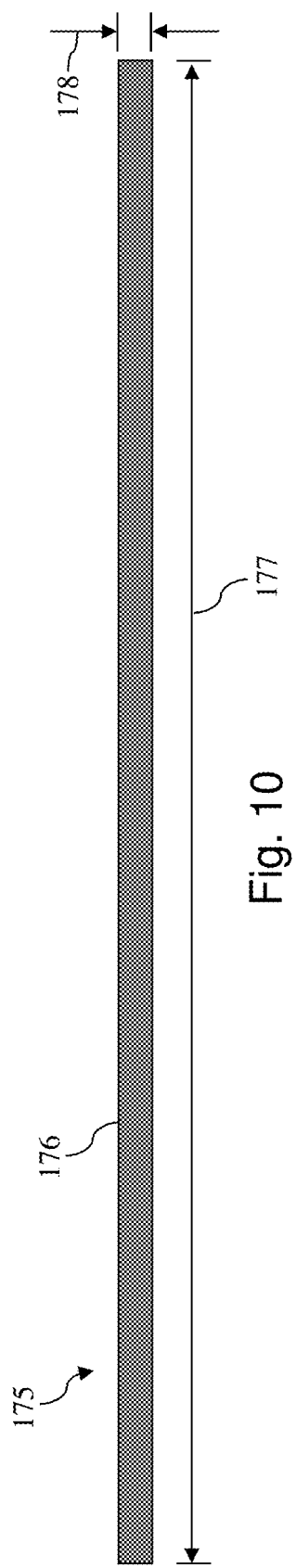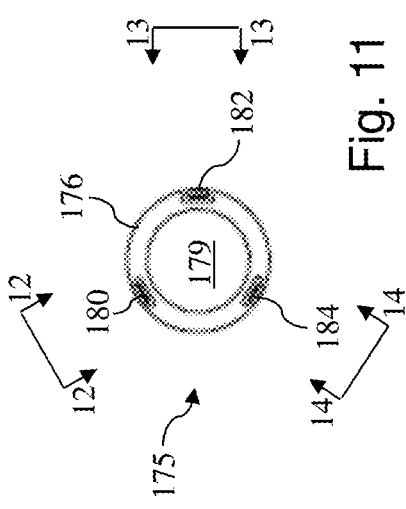

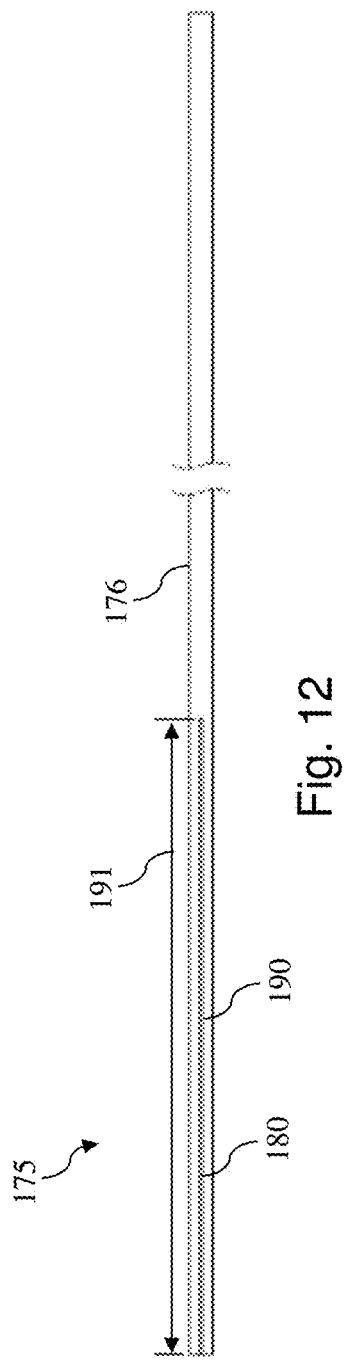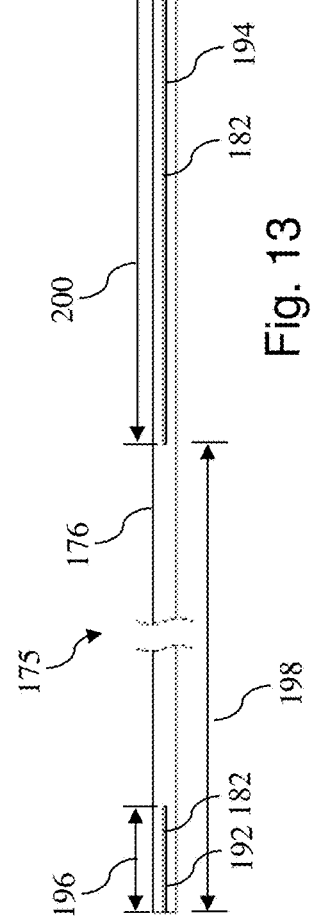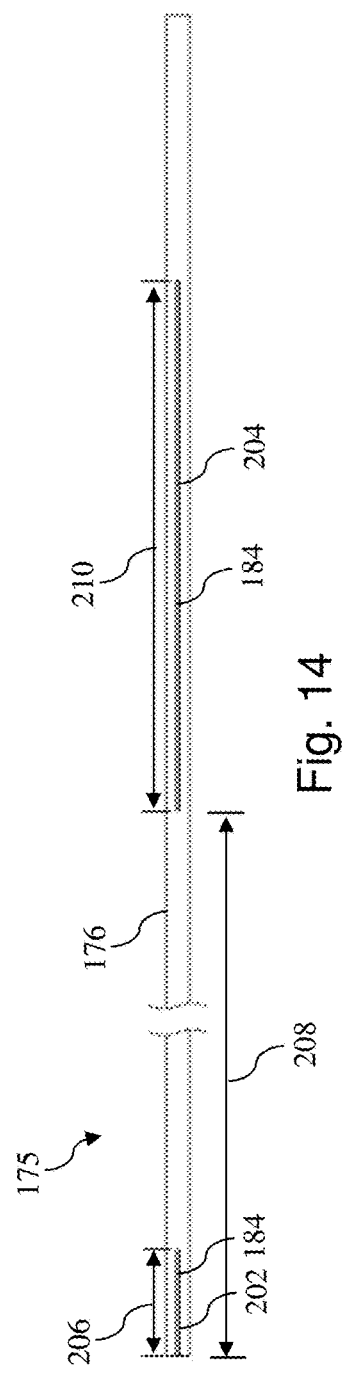

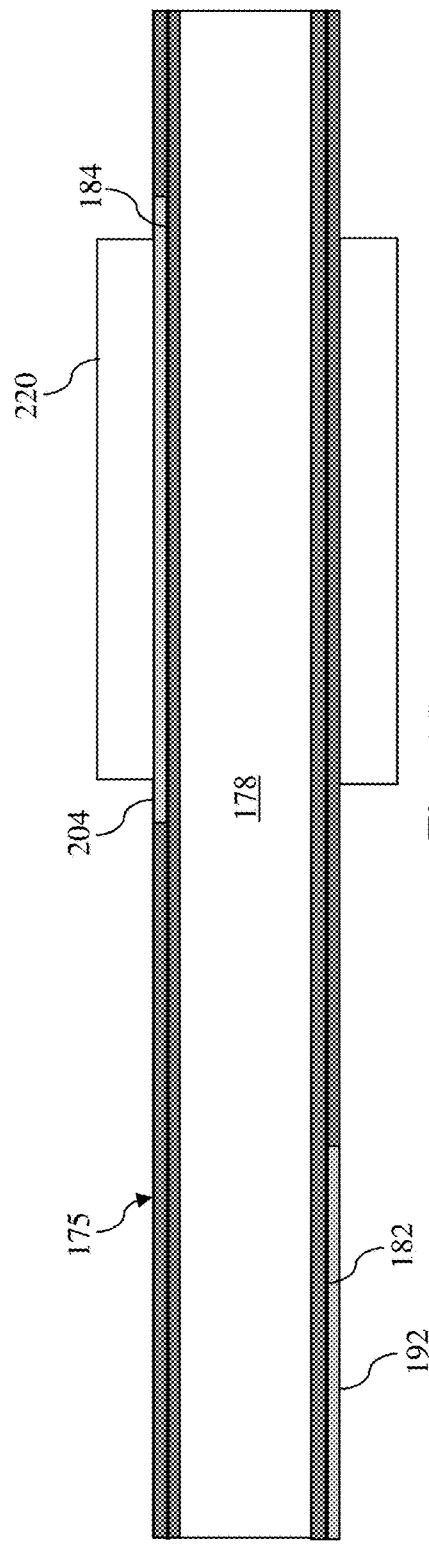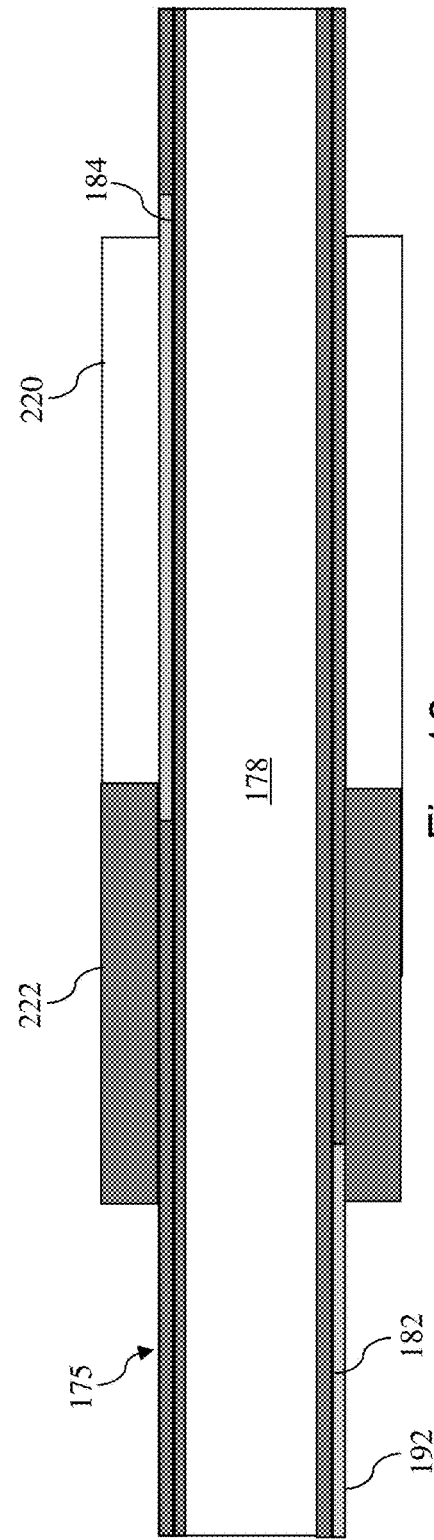

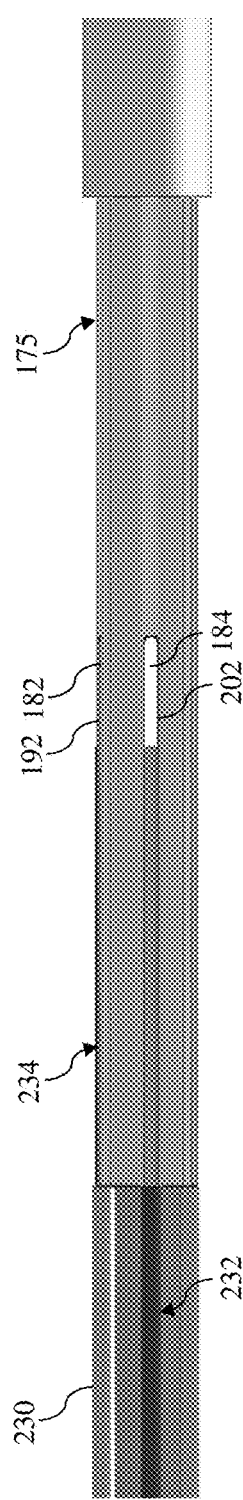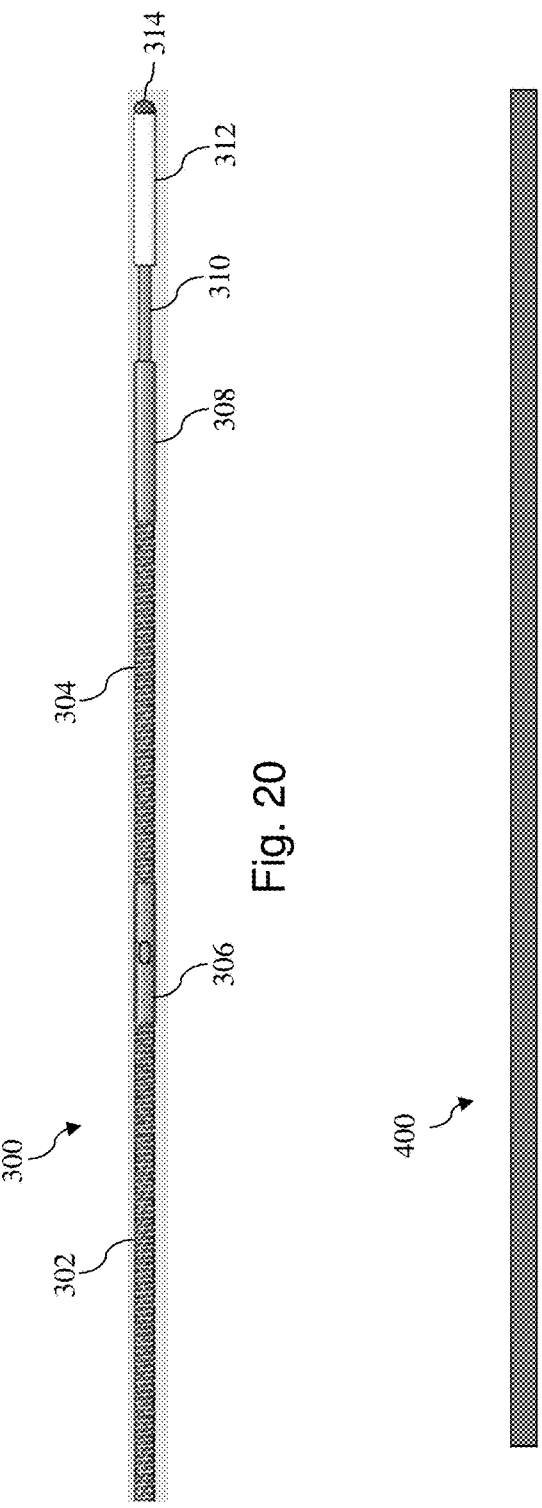
Fig. 19
Fig. 20
Fig. 21

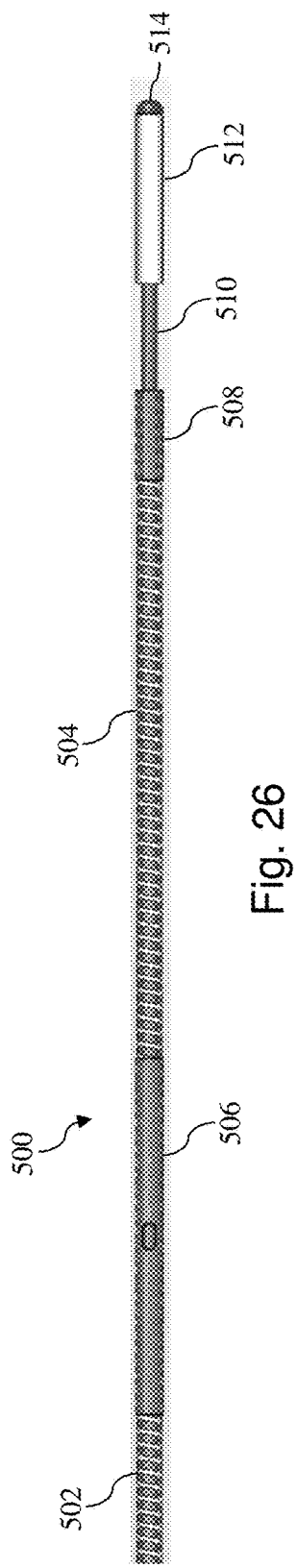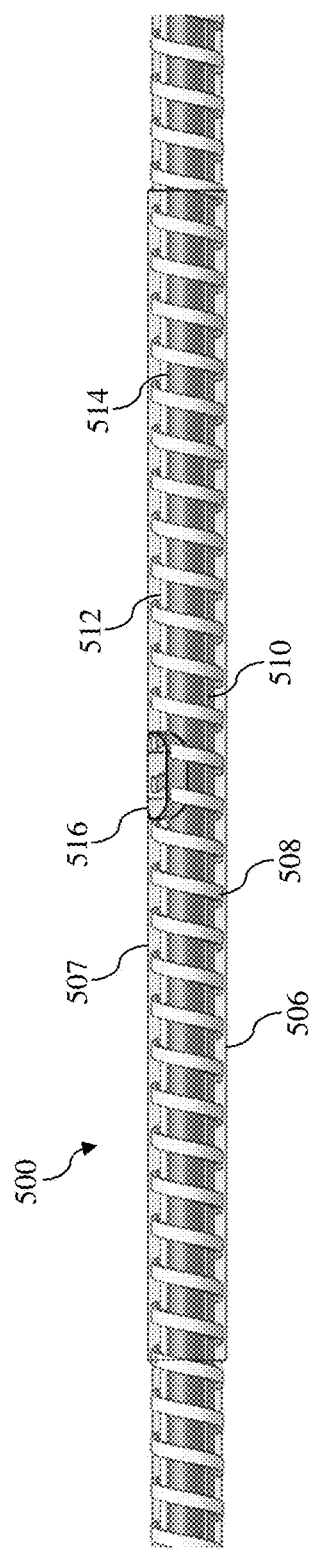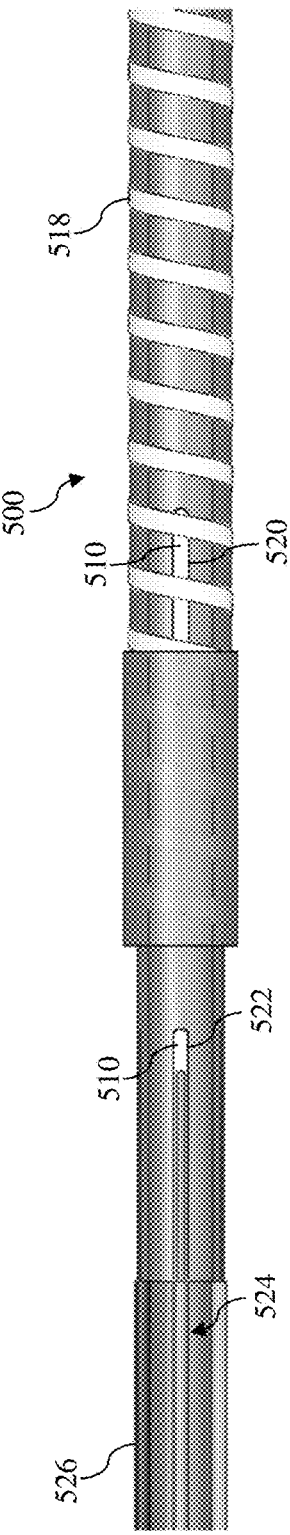
Fig. 26
Fig. 27
Fig. 28

CONNECTION STRUCTURES FOR INTRAVASCULAR DEVICES AND ASSOCIATED SYSTEMS AND METHODS

CROSS REFERENCE TO RELATED APPLICATIONS

The present application is a continuation of U.S. patent application Ser. No. 13/930,692, filed Jun. 28, 2013, now U.S. Pat. No. 9,750,417, which claims priority to and the benefit of U.S. Provisional Patent Application No. 61/665,739, filed Jun. 28, 2012, which are hereby incorporated by reference in their entireties.

TECHNICAL FIELD

The present disclosure relates to intravascular devices, systems, and methods. In some embodiments, the intravascular devices are guidewires that include one or more electronic components.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guidewires are utilized to measure the pressure within the blood vessel. To date, guidewires containing pressure sensors or other electronic components have suffered from reduced performance characteristics compared to standard guidewires that do not contain electronic components. For example, the handling performance of previous guidewires containing electronic components have been hampered, in some instances, by the limited space available for the core wire after accounting for the space needed for the conductors or communication lines of the electronic component(s), the stiffness of the rigid housing containing the electronic component(s), and/or other limitations associated with providing the functionality of the electronic components in the limited space available within a guidewire. Further, due to its small diameter, in many instances the proximal connector portion of the guidewire (i.e., the connector(s) that facilitate communication between the electronic component(s) of the guidewire and an associated controller or processor) is fragile and prone to kinking, which destroys the functionality of the guidewire. For this reason, surgeons are reluctant to remove the proximal connector from the guidewire during a procedure for fear of breaking the guidewire when reattaching the proximal connector. However, having the guidewire coupled to the proximal connector further limits the maneuverability and handling of the guidewire.

Accordingly, there remains a need for improved connectors and connector portions for use with intravascular devices (e.g., catheters and guidewires) that include one or more electronic components.

SUMMARY

Embodiments of the present disclosure are directed to intravascular devices, systems, and methods.

In some embodiments, methods of assembling an intravascular device are provided. In one embodiment, the method includes exposing a section of a first conductor embedded within tubular member; positioning a first conductive member around the tubular member adjacent to the exposed section of the first conductor; and electrically coupling the first conductive member to the first conductor. In some instances, the method further includes positioning a first insulating member around the tubular member adjacent to the first conductive member; positioning a second conductive member around the tubular member adjacent to the first insulating member such that the first insulating member is positioned between the first and second conductive members; and electrically coupling a second conductor embedded within the tubular member to the second conductive member. In some implementations, the method also includes exposing a section of the second conductor embedded within the tubular member, wherein the second conductive member is positioned around the tubular member adjacent to the exposed section of the second conductor.

Further, in some embodiments the method includes positioning a second insulating member around the tubular member adjacent to the second conductive member; positioning a third conductive member around the tubular member adjacent to the second insulating member such that the second insulating member is positioned between the second and third conductive members; and electrically coupling a third conductor embedded within the tubular member to the third conductive member. In some instances, the method further comprises exposing a section of the second conductor embedded within the tubular member, wherein the second conductive member is positioned around the tubular member adjacent to the exposed section of the second conductor; and exposing a section of the third conductor embedded within the tubular member, wherein the third conductive member is positioned around the tubular member adjacent to the exposed section of the third conductor.

In another embodiment, the method of assembling an intravascular device includes providing a polymer tubing having a plurality of conductors and a conductive coil embedded therein; exposing a first portion of the conductive coil embedded within the polymer tubing; exposing a first section of a first conductor of the plurality of conductors embedded within the polymer tubing; and electrically coupling the exposed first section of the first conductor to the exposed first portion of the conductive coil. In some instances, the method includes exposing a second portion of the conductive coil embedded within the polymer tubing;

exposing a first section of a second conductor of the plurality of conductors embedded within the polymer tubing; and electrically coupling the exposed first section of the second conductor to the exposed second portion of the conductive coil. Further, in some implementations the method also includes electrically isolating the first portion of the conductive coil from the second portion of the conductive coil. In that regard, electrically isolating the first portion of the conductive coil from the second portion of the conductive coil comprises forming an opening in a sidewall of the polymer tubing that severs a portion of the conductive coil positioned between the first and second portions of the conductive coil in some instances.

In some embodiment, electrical interfaces for an intravascular device are provided. In some embodiments, the electrical interfaces are formed using the methods described in the present disclosure.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 3 is a diagrammatic side view of a proximal connector portion of the intravascular device of FIG. 2 according to an embodiment of the present disclosure.

FIG. 4 is a diagrammatic side view of a proximal connector portion of an intravascular device of FIG. 2 similar to that of FIG. 3, but illustrating another embodiment of the present disclosure.

FIG. 6 is a diagrammatic side view of a proximal connector portion of the intravascular device of FIG. 5 according to an embodiment of the present disclosure.

FIG. 7 is a diagrammatic side view of a proximal connector portion of an intravascular device of FIG. 5 similar to that of FIG. 6, but illustrating another embodiment of the present disclosure.

FIG. 8 is a diagrammatic side view of a proximal connector portion of an intravascular device according to an embodiment of the present disclosure.

FIG. 9 is a diagrammatic side view of a portion of the proximal connector portion of FIG. 8 with inner components of the proximal connector portion illustrated.

FIG. 10 is a diagrammatic side view of an element for forming a component of the proximal connector portion of FIGS. 8 and 9 according to an embodiment of the present disclosure.

FIG. 11 is a diagrammatic cross-sectional end view of the element of FIG. 10.

FIG. 12 is a diagrammatic side view of the element of FIGS. 10 and 11 as viewed from section line 12-12 of FIG. 11.

FIG. 13 is a diagrammatic side view of the element of FIGS. 10-12 as viewed from section line 13-13 of FIG. 11.

FIG. 14 is a diagrammatic side view of the element of FIGS. 10-13 as viewed from section line 14-14 of FIG. 11.

Collectively, FIGS. 15-19 illustrate various aspects of assembling a proximal connector portion as illustrated in FIG. 8 according to an exemplary embodiment of the present disclosure.

FIG. 15 is a diagrammatic cross-sectional side view showing a conductive element being positioned over an element, such as the element shown in FIGS. 9-13, and electrically coupled to a conductor of the element according to an embodiment of the present disclosure.

FIG. 16 is a diagrammatic cross-sectional side view showing an insulating element being positioned over the element and adjacent to a distal portion of the conductive element of FIG. 15.

FIG. 17 is a diagrammatic cross-sectional side view showing another insulating element being positioned over the element and adjacent to a proximal portion of the conductive element of FIG. 15.

FIG. 18 is a diagrammatic cross-sectional side view showing another conductive element being positioned over the element and electrically coupled to another conductor of the element.

FIG. 19 is a diagrammatic side view showing a plurality of conductors associated with another element of an intravascular device being electrically coupled to the plurality of conductors of the element of FIG. 15.

FIG. 20 is a diagrammatic side view of a proximal connector portion of an intravascular device according to another embodiment of the present disclosure.

FIG. 21 is a diagrammatic side view of an element for forming a proximal connector portion of an intravascular device, such as the proximal connector portion of FIG. 20, according to an embodiment of the present disclosure.

FIG. 26 is a diagrammatic side view of a proximal connector portion of an intravascular device according to another embodiment of the present disclosure.

FIG. 27 is a diagrammatic side view of a portion of the proximal connector portion of FIG. 26 with inner components of the proximal connector portion illustrated.

FIG. 28 is a diagrammatic side view showing various electrical connections of the proximal connector portion of FIGS. 26 and 27 according to an embodiment of the present disclosure.

DETAILED DESCRIPTION

Figure 1:
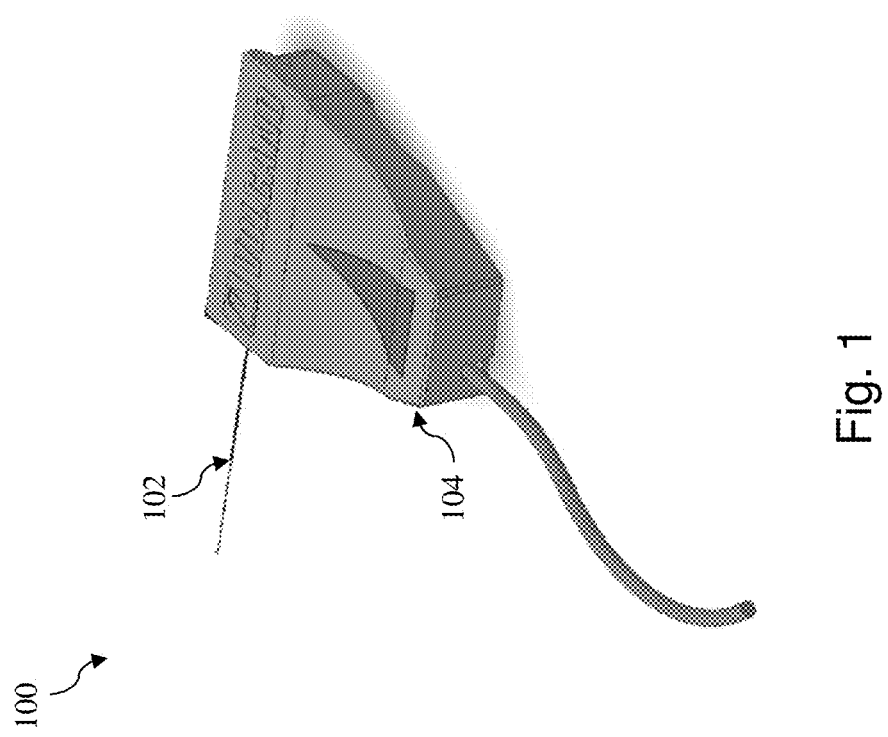
FIG. 1 is a diagrammatic perspective view of an intravascular system according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, intravascular catheters and intravascular guidewires. In that regard, intravascular catheters may or may not include a lumen extending along its length for receiving and/or guiding other instruments. If the intravascular catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a temperature sensor, an imaging element, an optical fiber, an ultrasound transducer, a reflector, a mirror, a prism, an ablation element, an fro electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized. Further, in some instances the flexible elongate member includes multiple electronic, optical, and/or electro-optical components (e.g., pressure sensors, temperature sensors, imaging elements, optical fibers, ultrasound transducers, reflectors, mirrors, prisms, ablation elements, RF electrodes, conductors, etc.).

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guidewire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm) and approximately 0.018" (0.4572 mm)). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Figure 2:
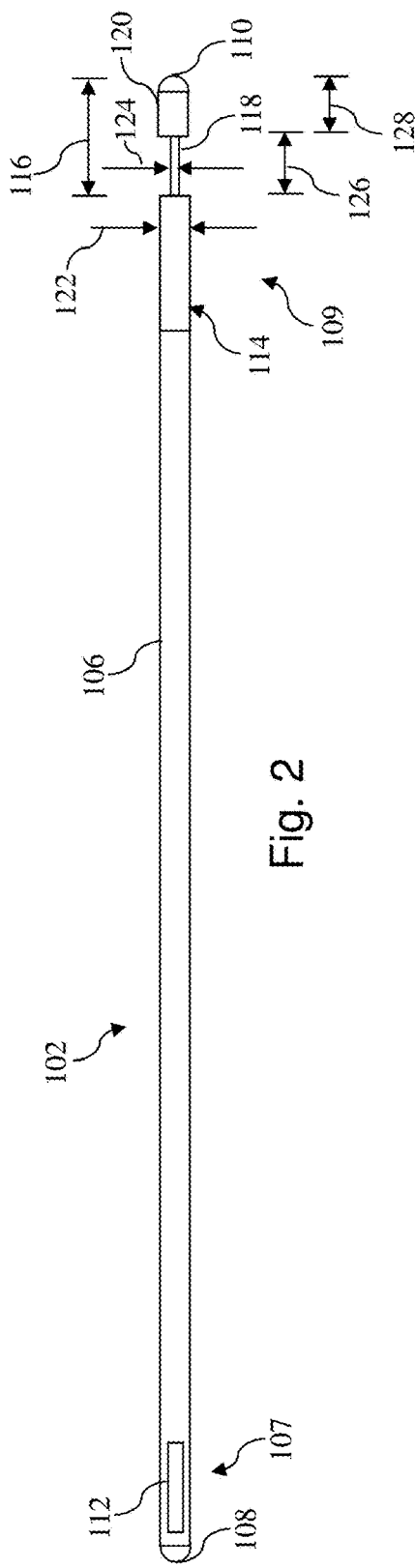
FIG. 2 is a diagrammatic side view of an intravascular device of the intravascular system of FIG. 1 according to an embodiment of the present disclosure.

Referring now to FIG. 1, shown therein is an intravascular system 100 according to an embodiment of the present disclosure. In that regard, the intravascular system includes an intravascular device 102 and a connector 104. Referring now to FIG. 2, a side view of the intravascular device 102 is provided according to an embodiment of the present disclosure. As shown, the intravascular device 102 includes a flexible elongate member 106 having a distal portion 107 adjacent a distal end 108 and a proximal portion 109 adjacent a proximal end 110. A component 112 is positioned within the distal portion 107 of the flexible elongate member 106 proximal of the distal tip 108. Generally, the component 112 is representative of one or more electronic, optical, or electro-optical components. In that regard, the component 112 is a pressure sensor, a temperature sensor, an imaging element, an optical fiber, an ultrasound transducer, a reflector, a mirror, a prism, an ablation element, an fro electrode, a conductor, and/or combinations thereof. The specific type of component or combination of components can be selected based on an intended use of the intravascular device. In some instances, the component 112 is positioned less than 10 cm, less than 5, or less than 3 cm from the distal tip 108. In some instances, the component 112 is positioned within a housing of the intravascular device 102. In that regard, the housing is a separate component secured to the flexible elongate member 106 in some instances. In other instances, the housing is integrally formed as a part of the flexible elongate member 106. In some embodiments, the flexible elongate member 106 comprises a stainless steel hypotube. Further, in some embodiments all or a portion of the flexible elongate member 106 is covered with a hydrophobic coating. In some particular embodiments, a polytetrafluoroethylene (PTFE) coating is utilized.

The intravascular device 102 also includes a connection portion 114 adjacent the proximal portion 109 of the device. In that regard, the connection portion 114 is spaced from the proximal end 110 of the flexible elongate member 106 by a distance 116. Generally, the distance 116 is between 0% and 50% of the total length of the flexible elongate member 106. While the total length of the flexible elongate member can be any length, in some embodiments the total length is between about 1300 mm and about 4000 mm, with some specific embodiments having a length of 1400 mm, 1900 mm, and 3000 mm. In some instances the connection portion 114 is spaced from the proximal end 110 between about 0 mm and about 1400 mm. In some specific embodiments, the connection portion 114 is spaced from the proximal end by a distance of 0 mm, 300 mm, and 1400 mm. Accordingly, in some instances the connection portion 114 is positioned at the proximal end 110. In some such embodiments, one or more aspects of the engagement and alignment features of the intravascular device 102 discussed below are positioned distal of the of the connection portion 114 instead of proximal of the connection portion 114 as shown in the embodiment of FIG. 2.

In that regard, in the illustrated embodiment of FIG. 2 the intravascular device 102 includes a section 118 extending proximally from the connection portion 114 to another section 120 that extends to proximal end 110. In the illustrated embodiment, the section 120 is rounded to proximal end 110. In other embodiments, the section 120 has a tapered, arcuate, and/or other changing profile as it extends proximally to proximal end 110. In that regard, in some instances the outer profile and/or diameter of the section 120 reduces as it extends proximally to proximal end 110 such that the reduced profile and/or diameter of the proximal end facilitates easier introduction of one or more other instruments over the intravascular device. In other embodiments, the section 120 has a constant profile as it extends proximally to proximal end 120.

As shown, the connection portion 114 has a diameter 122 (or other similar measurement for outer cross-section profiles for non-circular cross-sectional embodiments) while section 118 has a diameter 124 (again, or other similar measurement for outer cross-section profiles for non-circular cross-sectional embodiments). The diameter 124 of section 118 is different than the diameter 122 of connection portion 114. In that regard, the different sizes of the diameters 122, 124 creates a structure that is configured to facilitate alignment and/or connection of the intravascular device 102 to a connector, such as connector 104. In the illustrated embodiment, the diameter 124 of section 118 is less than the diameter 122 of the connection portion 114. In some embodiments, the diameter 124 of section 118 is between about 40% and about 80% of diameter 122, with some particular embodiments being about 42%, 64%, and/or other percentage of diameter 122. In that regard, in some embodiments the diameter 122 of connection portion 114 is between about 0.0178 mm and about 3.0 mm, with some particular embodiments being 0.3556 mm (0.014") and 0.4572 mm (0.018"). Accordingly, in some embodiments the diameter 124 of section 118 is between about 0.007 mm and about 2.4 mm, with some particular embodiments being 0.15 mm, 0.19 mm, 0.23 mm, and 0.29 mm. In the illustrated embodiment, the section 120 has a diameter that is approximately equal to diameter 122 and, therefore, greater than diameter 124. However, in other embodiments, section 120 has a diameter that is greater than diameter 122, less than diameter 122, greater than diameter 124, equal to diameter 124, and/or less than diameter 124.

As shown in FIG. 2, the section 118 extends proximally from connection portion 114 a distance 126, while section 120 extends proximally from section 118 to proximal end 110 a distance 128. Together, distances 126 and 128 equal the distance 116 that the connection portion 114 is spaced from the proximal end 110 of the intravascular device 102. In some instances, the distance 126 of is between about 0.508 mm (0.020") and about 2.54 mm (0.10"), with some particular embodiments being 0.762 mm (0.030"), 1.016 mm (0.040"), and 1.524 mm (0.060"). Further, while the transition between connection portion 114 and section 118 and the transition between section 118 and section 120 are shown as being stepped in the illustrated embodiments, in other embodiments the transitions are tapered and/or otherwise make a gradual change in outer diameter along the length of the intravascular device. In some embodiments, use of tapered and/or gradual transitions results in the proximal portion of the intravascular device 102 not having any sharp edges. In some implementations, the use of tapered and/or gradual transitions for one or both of the transitions between section 118 and either the connection portion 114 or section 120 makes cleaning the proximal portion of the device (e.g., to remove any liquids or other unwanted materials on the surface of the proximal portion of the intravascular device) easier. In some instances, sections 118 and 120 are formed as a separate assembly or component and subsequently joined to the connection portion 114 via suitable techniques, such as using solder, adhesive, mechanical connections, and/or combinations thereof.

The connection portion 114 is configured to facilitate communication between the intravascular device 102 and another device. More specifically, in some embodiments the connection portion 114 is configured to facilitate communication of data obtained by the component 112 to another device, such as a computing device or processor. Accordingly, in some embodiments the connection portion 114 is an electrical connector. In such instances, the connection portion 114 is configured to provide an electrical connection to one or more electrical conductors that extend along the length of the flexible elongate member 102 and are electrically coupled to the component 112. In some instances, the connection portion 114 includes one or more electrical connectors as described in U.S. Patent Application No. 61/665,697, titled "INTRAVASCULAR DEVICES, SYSTEMS, AND METHODS," filed Jun. 28, 2012, which is hereby incorporated by reference in its entirety. In other embodiments, the connection portion 114 includes an optical connector. In such instances, the connection portion 114 provides an optical connection to one or more optical communication pathways (e.g., fiber optic cable) that extend along the length of the flexible elongate member 106 and are optically coupled to the component 112. Further, in some embodiments the connection portion 114 provides both electrical and optical connections to both electrical conductor(s) and optical communication pathway(s) coupled to the component 112. In that regard, it should again be noted that component 112 is comprised of a plurality of elements in some instances. In some instances, the connection portion 114 is configured to provide a physical connection to another device, either directly or indirectly. In other instances, the connection portion 114 is configured to facilitate wireless communication between the intravascular device 102 and another device. Generally, any current or future developed wireless protocol(s) may be utilized. In yet other instances, the connection portion 114 facilitates both physical and wireless connection to another device.

As noted above, in some instances the connection portion 114 provides a connection between the component 112 of the intravascular device 102, 120 and an external device. Accordingly, in some embodiments one or more electrical conductors, one or more optical pathways, and/or combinations thereof extend along the length of the flexible elongate member 106 between the connection portion 114 and the component 112 to facilitate communication between the connection portion 114 and the component 112. Generally, any number of electrical conductors, optical pathways, and/or combinations thereof can extend along the length of the flexible elongate member 106 between the connection portion 114 and the component 112. In some instances, between one and ten electrical conductors and/or optical pathways extend along the length of the flexible elongate member 106 between the connection portion 114 and the component 112. For the sake of clarity and simplicity, the embodiments of the present disclosure described below include three electrical conductors and, therefore, the connection portion 114 is described as having three separate electrical connections corresponding to the three electrical conductors.

For example, as shown in FIG. 3, in some instances the connection portion 114 includes conductive portions 132, 134, and 136 that are separated from one another and the main body of the flexible elongate member 106 by insulating portions 138, 140, 142, and 144. In that regard, the conductive portions 132, 134, and 136 are formed of a conductive material and are portions of a hypotube, a coil, and/or combinations thereof in some instances. It is understood that the total number of communication pathways and/or the number of electrical conductors and/or optical pathways is different in other embodiments and, therefore, the number of conductive portions (or optical connectors) included in connection portion is different as well. More specifically, the number of communication pathways and the number of electrical conductors and optical pathways extending along the length of the flexible elongate member 106 is determined by the desired functionality of the component 112 and the corresponding elements that define component 112 to provide such functionality. As a result, the number and type of connections provided by connection portion 114 are likewise determined by the desired functionality of the component 112, the corresponding elements that define component 112 to provide such functionality, and the communication needs for such elements. Further still, in some instances, one or more of the insulating portions 138, 140, 142, and 144 is omitted. For example, as shown in the exemplary embodiment of FIG. 4, insulating portion 144 has been omitted.

Figure 5:
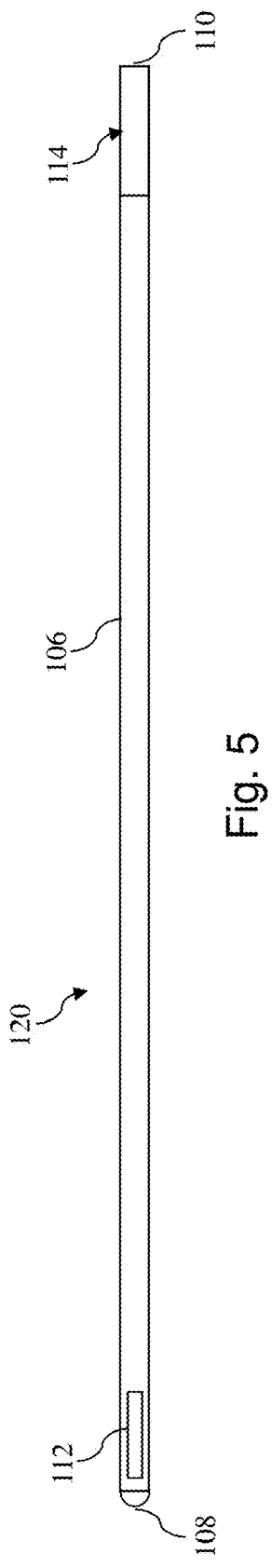
FIG. 5 is a diagrammatic side view of an intravascular device of the intravascular system of FIG. 1 similar to that of FIG. 2, but illustrating another embodiment of the present disclosure.

As noted above, in some instances the connection portion 114 is not spaced from the proximal end 110. For example, FIG. 5 illustrates an intravascular device 120 where the connection portion is positioned at the proximal end 110 of the intravascular device. In such embodiments, the proximal end 110 of the intravascular device 120 may be defined by an insulating element (as shown by insulating portion 144 in FIG. 6) or a conductive element (as shown by conductive portion 136 in FIG. 7). It should also be noted that while the arrangements of FIGS. 3, 4, 5, and 6 illustrate an insulating portion 138 as being positioned between the flexible elongate member 106 and the conductive portion 132, in some instances the conductive portion 132 is positioned immediately adjacent to the elongate member without insulating portion 138. Accordingly, the various embodiments and associated methods of forming connection portions for intravascular devices as discussed below may be implemented using any combination of the arrangement of features described above with respect to FIGS. 1-7.

Referring now to FIGS. 8 and 9, shown therein are aspects of a connector portion 150 of an intravascular device according to an embodiment of the present disclosure. As shown in FIG. 8, the connector portion 150 includes conductive portions 152, 154 and insulating portions 156, 158. In that regard, the insulating portion 156 separates the conductive portion 152 from the conductive portion 154. In some instances, the insulating portion 158 separates the conductive portion 152 from one or more other conductive portions (not shown) of the connector portion 150. A section 160 extending proximally from the connector portion 150 to another section 162 that extends to a proximal end 164. The sections 160, 162 have structures and arrangements as described above with respect to sections 118, 120 in some instances.

Referring now to FIG. 9, shown therein is a side view of part of the proximal connector portion 150. As shown, the insulating portion 158 includes an outer surface 166. A plurality of projections 168 extend from the outer surface 166. Generally, the connector portion 150 can include any number of projections 168 (or omit the projections entirely), but in some embodiments the connector portion 150 includes between 0 and 20 projections, with some particular embodiments having 0, 1, 5, and 8 projections. In some instances, the outer surface 166 has a generally cylindrical profile with a circular cross-section and the projections 168 also have a generally cylindrical profile with a circular cross-section, but with an increased outer diameter relative to the outer surface 166. In that regard, the outer diameter of the projections is between about 0.0127 mm (0.0005") and about 0.0762 mm (0.003") greater than the diameter of the outer surface 166 in some instances, with some particular embodiments being 0.0127 mm (0.0005"), 0.019 mm (0.00075"), and 0.0254 mm (0.001") greater. Accordingly, in some instances the outer surface 166 is recessed with respect to the projections 168 by a distance between about 0.0127 mm (0.0005") and about 0.0762 mm (0.003"), with some particular embodiments being recessed a distance of 0.0127 mm (0.0005"), 0.019 mm (0.00075"), and 0.0254 mm (0.001"). Surface portions 170 transition the insulating portion 158 between the outer surface 166 and the projections 168. In the illustrated embodiment, the surface portions 170 are tapered surfaces that extend at an oblique angle with respect to a longitudinal axis of the connector portion 150 between the outer surface 166 and the projections 168. In other embodiments, surface portions 170 are omitted such that a step is created at the transition between outer surface 166 and projections 168. In that regard, a surface extending between the outer surface 166 and the projections 168 extends perpendicular to the longitudinal axis of the connector portion 150 in some instances.

In the illustrated embodiment, the projections 168 have a length 172 along the longitudinal axis of the connector portion 150. The length 172 is between about 0.0508 mm (0.002") and about 1.27 mm (0.050") in some instances, with some particular embodiments having a length of 0.127 mm (0.005"), 0.254 mm (0.010"), and 0.508 mm (0.020"). Further, the projections 168 are spaced from another by a distance 174 along the longitudinal axis of the connector portion 150. The distance 174 can be any suitable distance and varies in some instances based on the number of projections utilized, lengths of the projections utilized, and/or other factors. In that regard, it is understood that the projections 168 may have equal spacing along the length of the connector portion 150, unequal spacing along the length of the connector portion 150, and/or a combination of equal and unequal spacing along the length of the connector portion.

In some instances, the projections 168 of insulating portion 156 are sized and shaped to prevent bridging between the conductive portions 152 and 154. In particular, the projections 168 are sized and shaped to minimize the impact of conductive liquid (e.g., blood or saline) bridging conductive portions 152 and 154 across insulating portion 156. Accordingly, in some particular embodiments the projections 168 are 0.010" wide such that the surface tension of any liquid in the portion(s) of the outer surface recessed relative to the projections (e.g., the portions defined by outer surface 166) will pull liquid off of the projection(s) 168 to minimize or eliminate any bridging.

The insulating portion 158 is positioned around a tubular member 175. In that regard, in some instances the diameter of an inner lumen of the insulating portion 158 is sized and shaped such that it can be slidingly advanced over the tubular member 175. Accordingly, in some instances, the diameter of the inner lumen of the insulating portion 158 is approximately equal to but slightly larger (e.g., between about 0.0005" and about 0.001" larger) than the outer diameter of the tubular member 175. Similarly, the conductive portion 152 is also positioned around the tubular member 175. In that regard, in some instances the diameter of an inner lumen of the conductive portion 152 is sized and shaped such that it can be slidingly advanced over the tubular member 175. Accordingly, in some instances, the diameter of the inner lumen of the conductive portion 152 is approximately equal to but slightly larger (e.g., between about 0.0005" and about 0.001" larger) than the outer diameter of the tubular member 175.

Referring now to FIGS. 10-14, additional features of the tubular member 175 will be described. Referring initially to FIG. 10, the tubular member 175 has a body 176 having a generally cylindrical profile. The body 176 has a length 177 and a diameter 178. In some instances, the length 177 is between about 12.7 mm (0.5") and about 76.2 mm (3.0"), with some particular embodiments having a length of 41.9 mm (1.65") and 33.0 mm (1.3"). In some implementations, the diameter 178 is between 0.0178 mm (0.0007") and about 0.4572 mm (0.018"). In some instances, the diameter of the inner lumen of the tubular member 175 is between about 0.0127 mm (0.0005") and about 0.4318 mm (0.017"). Accordingly, in some instances the tubular member 175 has a wall thickness between an outer surface of the body 176 and the inner surface defining the lumen between about 0.0127 mm (0.0005") and about 0.254 mm (0.01"), with some particular embodiments having a thickness of 0.0254 mm (0.001"), 0.04064 mm (0.0016"), 0.0508 mm (0.002"), and 0.08128 mm (0.0032"). In that regard, as discussed below the wall thickness of the tubular member 175 is sufficient to embed one or more conductors in some embodiments.

To that end, as shown in FIG. 11 the tubular member 175 has three conductors 180, 182, and 184 embedded within the wall of body 176. In the illustrated embodiment, the conductors 180, 182, and 184 are symmetrically and equally spaced about the circumference of the circular cross-section of the tubular member 175. Accordingly, the conductors 180, 182, and 184 are spaced from one another by about 120 degrees. In other embodiments, the conductors 180, 182, and 184 are not equally spaced about the circumference of the tubular member 175. Further, in some embodiments the tubular member 175 includes a greater number of conductors or a fewer number of conductors. In that regard, the number of conductors embedded within tubular member 175 is selected based on the desired functionality of the intravascular device, the number of conductive portions included on the proximal connector portion including the tubular member, and/or other factors. In that regard, it is understood that the conductors may be spaced symmetrically about the tubular member, spaced equally about the tubular member, spaced symmetrically and equally about the tubular member, not spaced equally or symmetrically about the tubular member, and/or combinations thereof. Further, in the illustrated embodiments the conductors 180, 182, and 184 run substantially parallel to a longitudinal axis of the tubular member 175 along the length of the tubular member. However, in other embodiments the one or more conductors embedded within the tubular member may be spiral wound, twisted, and/or otherwise extend along the length of the tubular member in a manner that is not parallel to the longitudinal axis of the tubular member.

The tubular member 175 is configured to be positioned around a core wire in some instances. To that end, in some embodiments the inner lumen 179 of the tubular member 175 is sized and shaped to receive the core wire and/or other communication line(s) of the intravascular device, such as conductor(s), optical, or otherwise. In the illustrated embodiment, however, the tubular member 175 includes conductors 180, 182, and 184 embedded within its wall such that the need to run conductors within the lumen 179 of the tubular member 175 can be eliminated in some implementations. Accordingly, the size of the core wire positioned within the lumen 179 of the tubular member 175 can be increased, allowing for the use of materials having a rigidity that is less than traditional stainless steel core wires, including without limitation shape memory alloys such as Nitinol and NiTiCo. Thus, in some instances, the core wire positioned within the tubular member 175 has an outer diameter between about 0.006" to 0.009".

In some embodiments, the body 177 of tubular member 175 is formed of an insulating material. In some embodiments, the insulating material is a polymer. The polymer used to form the body 177 of tubular member 175 is polyimide in some instances, but may be another suitable insulating material in other instances. The conductors 180, 182, and 184 can be formed of any suitable conductive material, including gold, an 80/20 platinum/iridium alloy, other platinum-iridium alloys, platinum-tungsten alloys, gold plated materials (e.g., stainless steel), copper alloy ribbon, copper alloy ribbon with silver, gold, and/or other plating, other suitable conductive materials, and/or combinations thereof. In some embodiments, the body 177 is formed of polyimide and the conductors 180, 182, and 184 are formed of a platinum-iridium compound. In one such embodiment, the platinum-iridium compound has a ratio of platinum to iridium of approximately 80/20. As will be discussed in greater detail below, by exposing one or more portions of each of the embedded conductors 180, 182, and 184, conductive elements of a proximal connector portion can be electrically coupled to the conductors 180, 182, and 184.

In that regard, referring now to FIGS. 12-14, an exemplary arrangement of exposed conductors 180, 182, and 184 suitable for use in a proximal connector portion of an intravascular device, such as proximal connector portion 150 is illustrated. Referring initially to FIG. 12, an elongated opening or recess 190 is formed in a sidewall of the body 177 of the tubular member 175 to expose underlying conductor 180. In that regard, any suitable technique can be used to remove the material of body 177 above the conductor 180, including without limitation laser ablation, chemical etching, and blade slitting. As shown, the opening 190 extends along the length of the body 177 from a distal end of the tubular member 175 a distance 191. In that regard, the distance 191 is between about 0.10" to 0.450" in some instances, with some particular embodiments being 0.150", 0.200" and 0.250". As will be discussed below, in some instances the distance 191 is selected to allow the conductor 180 to be electrically coupled to a conductive element associated with a flexible elongate member of an intravascular device adjacent the distal end of the tubular member and electrically coupled to a conductive element of a proximal connector portion. In the illustrated embodiment, the opening 190 has a substantially constant profile along its length. In particular, the opening 190 has a width that is constant along the length of the opening 190 that is sufficient to expose the conductor 180. The width of opening 190 may be greater than, less than, or equal to the width of conductor 180. In some instances, the width of the opening 190 is between about 0.0254 mm (0.001") and about 0.254 mm (0.01"), with some particular embodiments having a width of 0.0508 mm (0.002"). In other instances, the opening 190 has a variable profile along its length. In that regard, the size, shape, orientation, position around the circumference of the body 177 of the tubular member 175, and/or other aspect of the profile of the opening 190 varies along the length of the opening. In some instances, the profile of the opening 190 varies along the length of the opening based on characteristics of the embedded conductor 180.

Referring now to FIG. 13, elongated openings or recesses 192 and 194 are formed in the sidewall of the body 177 of the tubular member 175 to expose underlying conductor 182. In that regard, any suitable technique can be used to remove the material of body 177 above the conductor 182 to create openings 192 and 194, including without limitation laser ablation, chemical etching, and blade slitting. As shown, the opening 192 extends along the length of the body 177 from a distal end of the tubular member 175 a distance 196. In that regard, the distance 196 is between about 0.254 mm (0.01") and about 2.54 mm (0.1") in some instances, with some particular embodiments being 0.635 mm (0.025") and 1.27 mm (0.050"). As will be discussed below, in some instances the distance 196 is selected to allow the conductor 182 to be electrically coupled to a conductive element associated with a flexible elongate member of an intravascular device adjacent the distal end of the tubular member. In the illustrated embodiment, the opening 192 has a substantially constant profile along its length. In particular, the opening 192 has a width that is constant along the length of the opening 192 that is sufficient to expose the conductor 182. The width of opening 192 may be greater, less than, or equal to the width of conductor 182. In some instances, the width of the opening 192 is between about 0.0254 mm (0.001") and about 0.254 mm (0.01"), with some particular embodiments having a width of 0.0508 mm (0.002"). In other instances, the opening 192 has a variable profile along its length.

The opening 194 extends along the length of the body 177. In that regard, the opening 194 begins at a distance 198 from the distal end of the tubular member 175. The distance 198 varies depending on the particular implementation. For example, in some embodiments the distance 198 is determined based on the conductive band length, the insulator length, and/or the length of conductor 182 to be exposed. In the illustrated embodiment, the distance 198 is approximately 13.335 mm (0.525"), but can be larger or smaller in other instances. The opening 194 extends along the length of the body 177 a distance 200. In that regard, the distance 200 is between about 1.27 mm (0.050") and about 10.16 mm (0.400") in some instances, with some particular embodiments being 2.54 mm (0.10"), 3.81 mm (0.150"), and 5.08 mm (0.20"). As will be discussed below, in some instances the distance 200 is selected to allow the conductor 182 to be electrically coupled to a conductive element of a proximal connector portion of a flexible elongate member. In the illustrated embodiment, the opening 194 has a substantially constant profile along its length. In particular, the opening 194 has a width that is constant along the length of the opening 194 that is sufficient to expose the conductor 182. The width of opening 194 may be greater than, less than, or equal to the width of conductor 182. In some instances, the width of the opening 194 is between 0.0254 mm (0.001") and about 0.254 mm (0.01"), with some particular embodiments having a width of 0.0508 mm (0.002"). In other instances, the opening 194 has a variable profile along its length. In that regard, the size, shape, orientation, position around the circumference of the body 177 of the tubular member 175, and/or other aspect of the profile of the opening 194 varies along the length of the opening. In some instances, the profile of the opening 194 varies along the length of the opening based on characteristics of the embedded conductor 182.

Referring now to FIG. 14, elongated openings or recesses 202 and 204 are formed in the sidewall of the body 177 of the tubular member 175 to expose underlying conductor 184. In that regard, any suitable technique can be used to remove the material of body 177 above the conductor 184 to create openings 202 and 204, including without limitation laser ablation, chemical etching, and blade slitting. As shown, the opening 202 extends along the length of the body 177 from a distal end of the tubular member 175 a distance 206. In that regard, the distance 206 is between about 0.254 mm (0.01") and about 2.54 mm (0.1") in some instances, with some particular embodiments being 0.635 mm (0.025") and 1.27 mm (0.050"). In some instances, the distance 206 is equal to the distance 196. As will be discussed below, in some instances the distance 206 is selected to allow the conductor 184 to be electrically coupled to a conductive element associated with a flexible elongate member of an intravascular device adjacent the distal end of the tubular member. In the illustrated embodiment, the opening 202 has a substantially constant profile along its length. In particular, the opening 202 has a width that is constant along the length of the opening 202 that is sufficient to expose the conductor 184. The width of opening 202 may be greater than, less than, or equal to the width of conductor 184. In some instances, the width of the opening 202 is between about 0.0254 mm (0.001") and about 0.254 mm (0.01"), with some particular embodiments having a width of 0.0508 mm (0.002"). In other instances, the opening 202 has a variable profile along its length.

The opening 204 extends along the length of the body 177. In that regard, the opening 204 begins at a distance 208 from the distal end of the tubular member 175. The distance 208 varies depending on the particular implementation. For example, in some embodiments the distance 208 is determined based on the conductive band length, the insulator length, and/or the length of conductor 184 to be exposed. In the illustrated embodiment, the distance 208 is approximately 27.305 mm (1.075"), but can be larger or smaller in other instances. The opening 204 extends along the length of the body 177 a distance 210. In that regard, the distance 210 is between about 1.27 mm (0.050") and about 10.16 mm (0.400") in some instances, with some particular embodiments being 2.54 mm (0.10"), 3.81 mm (0.150"), and 5.08 mm (0.20"). As will be discussed below, in some instances the distance 210 is selected to allow the conductor 184 to be electrically coupled to a conductive element of a proximal connector portion of a flexible elongate member. In the illustrated embodiment, the opening 204 has a substantially constant profile along its length. In particular, the opening 204 has a width that is constant along the length of the opening 204 that is sufficient to expose the conductor 184. The width of opening 204 may be greater than, less than, or equal to the width of conductor 184. In some instances, the width of the opening 204 is between about 0.0254 mm (0.001") and about 0.254 mm (0.01"), with some particular embodiments having a width of 0.0508 mm (0.002"). In other instances, the opening 204 has a variable profile along its length. In that regard, the size, shape, orientation, position around the circumference of the body 177 of the tubular member 175, and/or other aspect of the profile of the opening 204 varies along the length of the opening. In some instances, the profile of the opening 204 varies along the length of the opening based on characteristics of the embedded conductor 184.

Referring now to FIGS. 15-19, shown therein are various aspects of assembling a proximal connector portion, such as connector portion 150 illustrated in FIGS. 8 and 9, according to an exemplary embodiment of the present disclosure. Referring initially to FIG. 15, a conductive element 220 is positioned around tubular member 175. In particular, conductive element 220 is positioned around tubular member 175 such that conductive element 220 is positioned in proximity to opening 204 such that the conductive element 220 can be electrically coupled to the conductor 184. As shown, the conductive element 220 is positioned coaxially around the tubular member 175 in the illustrated embodiment. In some instances, such as the embodiment of FIG. 15, the conductive element 220 is positioned around tubular member 175 such that a portion of the opening 204 extends proximal of the conductive element 220 and a portion of the opening 204 extends distal of the conductive element. In that regard, positioning the conductive element 220 around the tubular member 175 and over the opening 204 results in a space between the conductive element 220 and the conductor 184 being defined. In some instances, the space defined between the conductive element 220 and the conductor 184 is suitable for introducing solder or other flowable conductive material into the space such that when the solder or other flowable conductive material solidifies an electrical connection between the conductive element 220 and the conductor 184 is created. In some particular instances, solder is flowed through the space from the portion(s) of the opening 204 exposed proximal and/or distal of the conductive element 220 towards the middle of the conductive element 220. In some instances, a conductive adhesive is utilized instead of solder. While the conductive element 220 is positioned around tubular member 175 such that portions of the opening 204 extend both proximal and distal of the conductive element 220 in the illustrated embodiment, in other embodiments the conductive element 220 is positioned such that the opening 204 is exposed either proximal or distal of the conductive element, but not both. In such instances, the solder (or conductive adhesive) is flowed into the space between the conductor 184 and the conductive element 220 from the exposed portion of the opening 204 that is either proximal or distal of the conductive element.

Referring to FIG. 16, an insulating member 222 is positioned around the tubular member 175. As shown, the insulating member 222 is positioned coaxially around the tubular member 175. In some embodiments, the insulating member 260 is advanced proximally along the tubular member 175 from a distal end of the tubular member 175 until the insulating member 222 is positioned adjacent the distal end of the conductive element 220. In some embodiments, the insulating member 222 is advanced along the tubular member 175 until a proximal end of the insulating member 222 contacts a distal end of the conductive element 220. In some instances, the insulating member 222 is secured to the tubular member 175 by an adhesive. In other instances, the insulating member 222 is not directly secured to the tubular member 175, but is held in place by surrounding elements of the proximal connector portion that are secured to the tubular member 175, such as conductive elements that are electrically coupled to the conductors of the tubular member.

Figure 17:
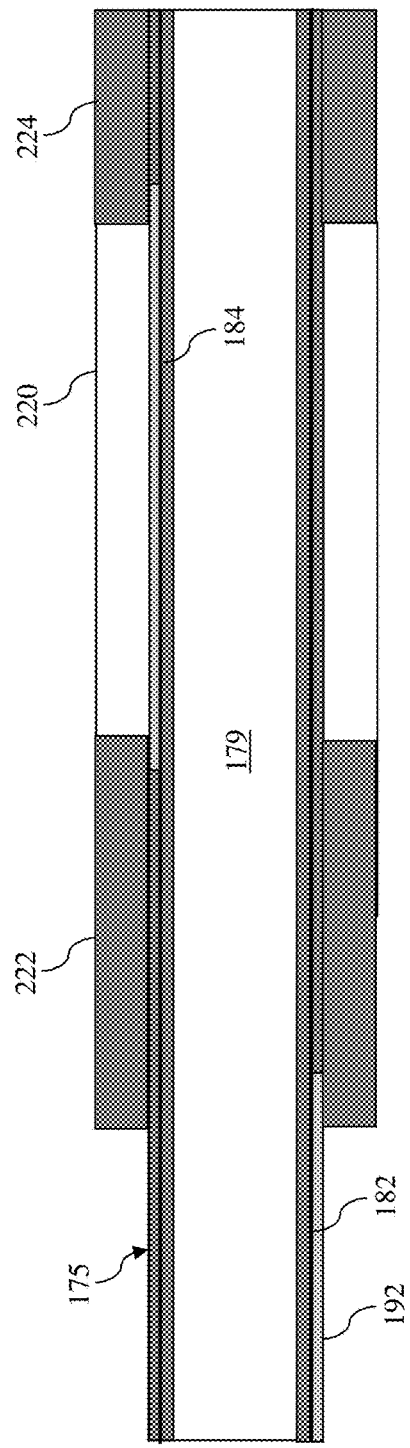

Referring now to FIG. 17, in some instances an insulating member 224 is optionally positioned around the tubular member 175 proximal of the conductive element 220. As shown, the insulating member 224 is positioned coaxially around the tubular member 175 in the illustrated embodiment. In some embodiments, the insulating member 260 is advanced distally along the tubular member 175 from a proximal end of the tubular member 175 until the insulating member 224 is positioned adjacent the proximal end of the conductive element 220. In some embodiments, the insulating member 224 is advanced along the tubular member 175 until a distal end of the insulating member 224 contacts a proximal end of the conductive element 220. In some instances, the insulating member 224 is secured to the tubular member 175 by an adhesive. In other instances, the insulating member 222 is not directly secured to the tubular member 175, but is held in place by surrounding elements of the proximal connector portion that are secured to the tubular member 175, such as conductive elements that are electrically coupled to the conductors of the tubular member. Further, in some implementations the insulating member 224 is omitted from the proximal connector portion of the intravascular. Further still, in some embodiments the insulating member 224 is positioned around and secured to the tubular member 175 prior to the conductive element 220.

Figure 18:
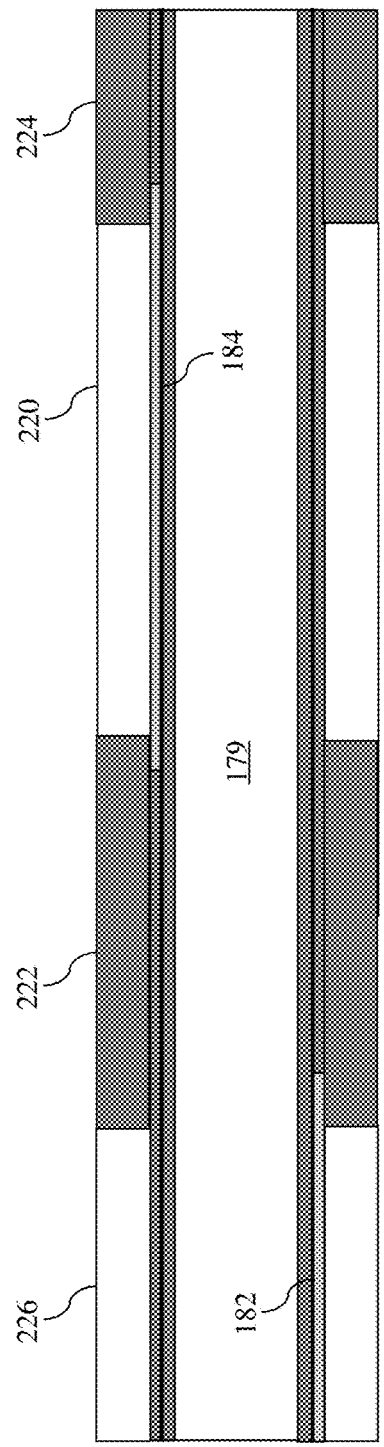

Referring to FIG. 18, a conductive element 226 is positioned around tubular member 175. In particular, conductive element 226 is positioned around tubular member 175 such that conductive element 226 is positioned in proximity to opening 192 such that the conductive element 226 can be electrically coupled to the conductor 182. As shown, the conductive element 226 is positioned coaxially around the tubular member 175 in the illustrated embodiment. In some embodiments, the conductive element 226 is advanced proximally along the tubular member 175 from a distal end of the tubular member 175 until the conductive element 226 is positioned adjacent the distal end of the insulating member 222. In some embodiments, the conductive element 226 is advanced along the tubular member 175 until a proximal end of the conductive element 226 contacts a distal end of the insulating member 222.

In some instances, the conductive element 226 is positioned around tubular member 175 such that a portion of the opening 192 extends distal of the conductive element 226. In some instances, a portion of the opening 192 also extends proximal of the conductive element 226. In that regard, positioning the conductive element 226 around the tubular member 175 and over the opening 192 results in a space between the conductive element 226 and the conductor 182 being defined. In some instances, the space defined between the conductive element 222 and the conductor 182 is suitable for introducing solder or other flowable conductive material into the space such that when the solder or other flowable conductive material solidifies an electrical connection between the conductive element 226 and the conductor 182 is created. In some particular instances, solder is flowed through the space from the portion of the opening 192 exposed distal of the conductive element 226 towards the middle and proximal portions of the conductive element 226. In some instances, a conductive adhesive is utilized instead of solder. Steps similar to those of FIGS. 15-18 can be repeated to form a proximal connector portion with any number of conductive elements electrically coupled to conductors of the tubular member 175.

Referring now to FIG. 19, shown therein is a plurality of conductors associated with another element 230 of an intravascular device, such as flexible elongate member 106 and/or a core wire of the flexible elongate member 106, being electrically coupled to the conductors 180, 182, and 184 of tubular member 175. In particular, the openings 190, 192, and 202 of the tubular member (illustrated in FIGS. 12-14, respectively) provide access to the conductors 180, 182, and 184 adjacent the distal end of the tubular member 175. Accordingly, the conductors associated with element 230 can be electrically coupled to the conductors 180, 182, and 184 using the openings 190, 192, and 202. In that regard, FIG. 19 shows the electrical coupling of two of the three conductors associated with element 230, particularly conductors 232 and 234, to conductors 184 and 182 of tubular member 175, respectively. However, it is understood that the third conductor associated with element 230 is likewise electrically coupled to conductor 180. In that regard, in some embodiments the element 230 includes the same number of conductors as tubular member 175 such that there is a 1-to-1 correspondence of the conductors associated with element 230 and those embedded within tubular member 175.

However, in some instances, the element 230 includes the more or less conductors than tubular member 175. Where the element 230 includes more conductors than tubular member 175, more than one conductor of element 230 may be connected to a single conductor of tubular member 175 and/or one or more conductors of element 230 are not connected to a conductor of the tubular member 175. In some instances, one or more conductors associated with element 230 that are not connected to conductors embedded within the tubular member extend along the lumen 179 of tubular member 175 and pass through an opening in the sidewall of the tubular member. For example, in some instances in addition to coupling one or more conductors of element 230 to one or more conductors embedded within tubular member 175, one or more conductors are passed through an opening in a sidewall of the tubular member as described in U.S. Patent Application No. 61/665,711, titled "CONNECTION STRUCTURES FOR INTRAVASCULAR DEVICES AND ASSOCIATED SYSTEMS AND METHODS," filed Jun. 28, 2012, and hereby incorporated by reference in its entirety. Where the element 230 includes fewer conductors than tubular member 175, one or more conductors of element 230 may be connected to two or more conductors of tubular member 175 and/or one or more conductors of tubular member 175 are not connected to a conductor of the element 230.

The conductors associated with element 230 are electrically coupled to the conductors of tubular member 175 using any suitable technique, including soldering, plasma welding, and/or resistance welding. In some instances, a proximal section of each conductor associated with element 230 has any insulating coating or sheath removed to expose the underlying conductive core. The conductive core is positioned within a corresponding opening formed in the distal end of the tubular member 175 such that the conductive core is contact with or at least close proximity to a conductor of the tubular member.

Referring now to FIG. 20, shown therein is a proximal connector portion 300 according to another embodiment of the present disclosure. As shown, the connector portion 300 includes conductive portions 302, 304 and at least one insulating portion 306. In that regard, the insulating portion 306 separates the conductive portion 302 from the conductive portion 304. In some instances, portion 308 is also an insulating portion. However, in other instances portion 308 is electrically coupled to conductive portion 304. A section 310 extends proximally from the connector portion 300 to another section 312 that extends to a proximal end 314. The sections 310, 312 have structures and arrangements as described above with respect to sections 160, 162 of proximal connector portion 150 in some instances. In some instances, at least the conductive portions 302, 304 and insulating portion 306 are formed from a single tubular member having an embedded conductive coil as described below.

Referring now to FIGS. 21-25, shown therein are features related to forming a proximal connector portion of an intravascular device, such as connector portion 300, according to an embodiment of the present disclosure. Referring initially to FIG. 21, shown therein is tubing 400. In that regard, tubing 400 is a polymer tubing that includes a conductive coil embedded therein. The polymer used to form tubing 400 is polyimide in some instances, but may be another suitable insulating material in other instances. The conductive coil can be formed of any suitable conductive material, including gold, an 80/20 platinum/iridium alloy, other platinum-iridium alloys, platinum-tungsten alloys, gold plated materials (e.g., stainless steel), other suitable conductive materials, and/or combinations thereof. In some embodiments, tubing 400 is a polyimide tubing with an embedded spiral ribbon coil formed of a platinum-iridium compound. In one such embodiment, the platinum-iridium compound has a ratio of platinum to iridium of approximately 80/20. As will be discussed in greater detail below, by exposing one or more portions of the embedded coil and electrically isolating the exposed portions from one another one or more conductive connectors can be defined in the tubing 400.

Figure 22:
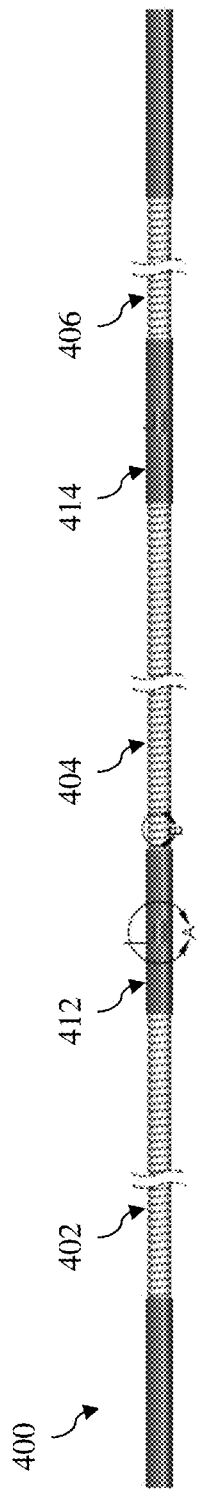
FIG. 22 is a diagrammatic side view of part of a proximal connector portion formed from the element of FIG. 21 according to an embodiment of the present disclosure.
Figure 23:
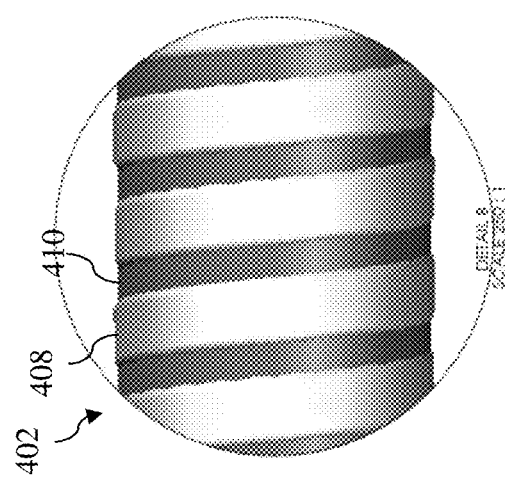
FIG. 23 is a diagrammatic close-up side view of a conductor portion of the proximal connector portion of FIG. 22.

For example, as shown in FIG. 22, three conductive connectors 402, 404, and 406 have been formed by removing the surrounding polymer to expose the underlying coil. In that regard, the polymer is removed by laser ablation and/or chemical etching. As shown in FIG. 23, the polymer is removed such that the exposed portion of the coil 408 extends above the remaining polymer 410. In some instances, the polymer is removed such that the exposed coils 408 extend between about 0.0001" and about 0.0005" above the polymer. In one particular embodiment, the polymer is removed such that the exposed coils 408 extend approximately 0.0002" above the polymer. In other instances, the polymer is removed such that the exposed portion of the coil 408 and the remaining polymer 410 are substantially aligned with one another.

Figure 25:
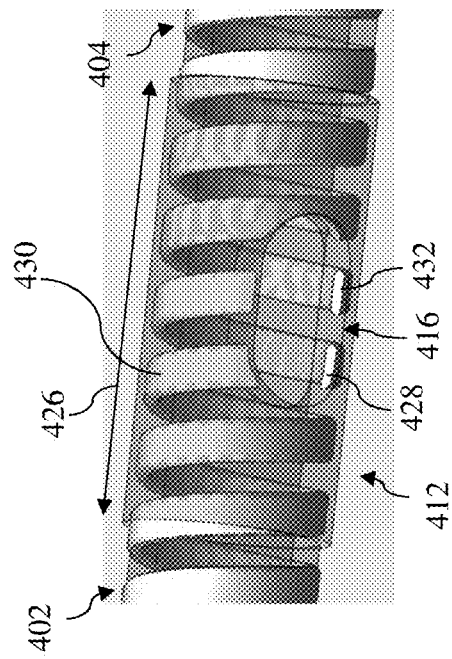
FIG. 25 is a diagrammatic close-up, partial phantom perspective view of an insulator portion of the proximal connector portion of FIG. 22.
Figure 24:
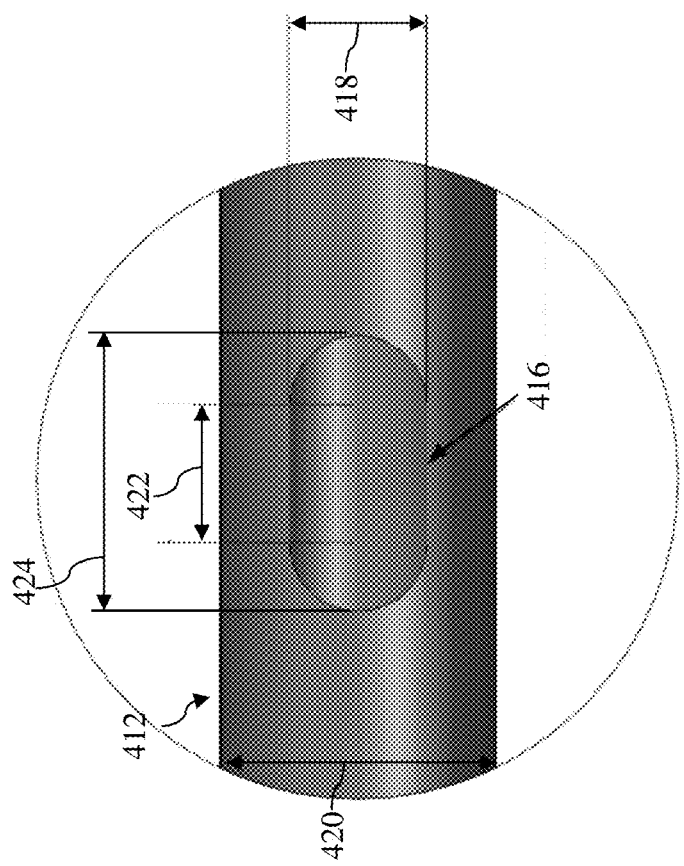
FIG. 24 is a diagrammatic close-up side view of an insulator portion of the proximal connector portion of FIG. 22.

Referring again to FIG. 22, in addition to exposing the connectors 402, 404, and 406, it is necessary to electrically isolate the connectors from one another. In that regard, the connectors 402, 404, and 406 are portions of the same coil embedded in tubing 400. Accordingly, it is necessary to separate the connectors 402, 404, and 406 from one another if they are to act as separate connectors. In that regard, isolation region 412 is positioned between connectors 402 and 404, while isolation region 414 is positioned between connectors 404 and 406. One technique for electrically isolating the connectors is illustrated by the detailed views of isolation region 412 provided in FIGS. 24 and 25. As shown in FIGS. 24 and 25, the isolation region 412 includes an opening 416 through a sidewall of the tubing 400. In that regard, in the illustrated embodiment the opening 416 is generally pill shaped, having elongated straight sides and rounded ends. In that regard, the opening 416 has a height 418 that is generally between about 25% and about 60% of a diameter 420 of the tubing 400. In one particular embodiment, the tubing 400 has an outer diameter of 0.014" and the opening 416 has a height 418 of 0.0070". In the illustrated embodiment, opening 416 also has a length 422 associated with the straight sides and an overall length 424 that includes the rounded end portions. Generally, the length 422 is between about 5% and about 90% of a total length 426 of the isolation region 412, while the length 424 is between about 10% and about 95% of the total length of the isolation region. In that regard, the size of the opening is dependent upon ensuring that at least one full coil wind has been separated so that there is definitive coil isolation. Accordingly, in some instances the opening has a minimum length of 2.5 times the coil pitch. For example, if the coil pitch is 0.005, then the opening length would be ~0.0125", thus guaranteeing that at least 1 full coil wind was separated.

As shown in FIG. 25, by creating the opening 416 in the side wall portions of the imbedded coil are also removed. In that regard, the opening 416 is created by laser cutting. In the illustrated embodiment, two windings of the coil have been cut. In other embodiments, one or more than two windings of the coil are cut within the isolation region 412. As a result of cutting two windings, three winding portions are created, namely coil portion 428 that is positioned within isolation portion 412, coil portion 430 that extends to the exposed portion that forms connector 402, and coil portion 432 that extends to the exposed portion that forms connector 404. In this manner, the coil portions 430 and 432 are electrically isolated from each other such that they can serve as separate electrical connectors for an intravascular device.

Referring now to FIG. 26, shown therein is a proximal connector portion 500 according to another embodiment of the present disclosure. As shown, the connector portion 500 includes conductive portions 502, 504 and at least one insulating portion 506. In that regard, the insulating portion 506 separates the conductive portion 502 from the conductive portion 504. In some instances, portion 508 is also an insulating portion. However, in other instances portion 508 is electrically coupled to conductive portion 504. A section 510 extends proximally from the connector portion 500 to another section 512 that extends to a proximal end 514. The sections 510, 512 have structures and arrangements as described above with respect to sections 160, 162, 310, and 312 in some instances. In some instances, at least the conductive portions 502, 504 and insulating portion 506 are formed from one or more tubular members having embedded conductors and/or an embedded conductive coil as described below. In that regard, in some embodiments the connector portion 500 is a combination of the features and associated manufacturing/assembly steps of connector portions 150 and 300 described above in the context of FIGS. 8-25.

For example, as shown in FIG. 27, the connector portion 500 includes a tubing 507 having a conductive coil 508 embedded therein, similar to tubing 400 described above. However, the connector portion 500 also includes a plurality of conductors embedded therein that extend along the length of the connector portion 500, similar to conductors 180, 182, and 184 of tubular member 175 described above. In FIG. 27, two of the three conductors, conductors 510 and 512, are shown. In some instances, the conductive coil 508 and the conductors 510 and 512 are embedded within the same tubing 507. In some such embodiments, the conductive coil 508 is positioned radially outward from the conductors 510, 512 such that the conductive coil is separated from the conductors 510, 512 by the insulating material of the tubing. In this manner, the conductive coil 508 is electrically isolated from the conductors. In other embodiments, the conductive coil 508 is embedded within one tubing and the conductors 510, 512 are embedded within a separate tubing. In such embodiments, the tubing with the conductive coil includes a central lumen that is sized and shaped to receive the tubing with the conductors 510, 512. For example, in some embodiments the tubing with the conductors 510, 512 is slidably received within the tubing with the conductive coil.

Referring now to FIGS. 27 and 28, the electrical conductors 510, 512 are electrically coupled to exposed portions of the conductive coil 508 to define conductive portions, such as conductive portions 502 and 504, of the of the proximal connector 500. In that regard, it is understood that sections of the conductive coil 508 are exposed and electrically isolated from one another using techniques similar to those described above in the context of tubing 400. For example, as shown in FIG. 27, opening 516 electrically isolates the conductive portion 502 from the conductive portion 504. Similarly, in the illustrated embodiment of FIG. 28, coil section 518 has been exposed by removing an outer portion of the tubing 507. Likewise, it is understood that the electrical conductors 510, 512 are exposed using techniques similar to those described above in the context of tubular member 175. For example, openings 520 and 522 are formed within the tubing to expose the underlying conductor 510. Where the conductive coil 508 and electrical conductors 510, 512 are embedded within a common tubing, laser ablation or other suitable technique for removing portions of the tubing between the conductors 510, 512 and the conductive coil 508 is utilized to form a space between the conductors 510, 512 and the conductive coil 508 into which solder or other flowable conductive material can be introduced to electrically couple the conductors 510, 512 to the conductive coil. For example, as shown in FIG. 28, in some instances solder is introduced into the space between conductor 510 and coil section 518 resulting from opening 520. Where the conductive coil 508 and electrical conductors 510, 512 are embedded within separate tubing components, appropriate portions of each tubing are removed prior to assembling the tubings together (e.g., inserting the tubing containing conductors 510, 512 within the tubing containing conductive coil 508) and/or after assembling the tubings together.

Figure 29:
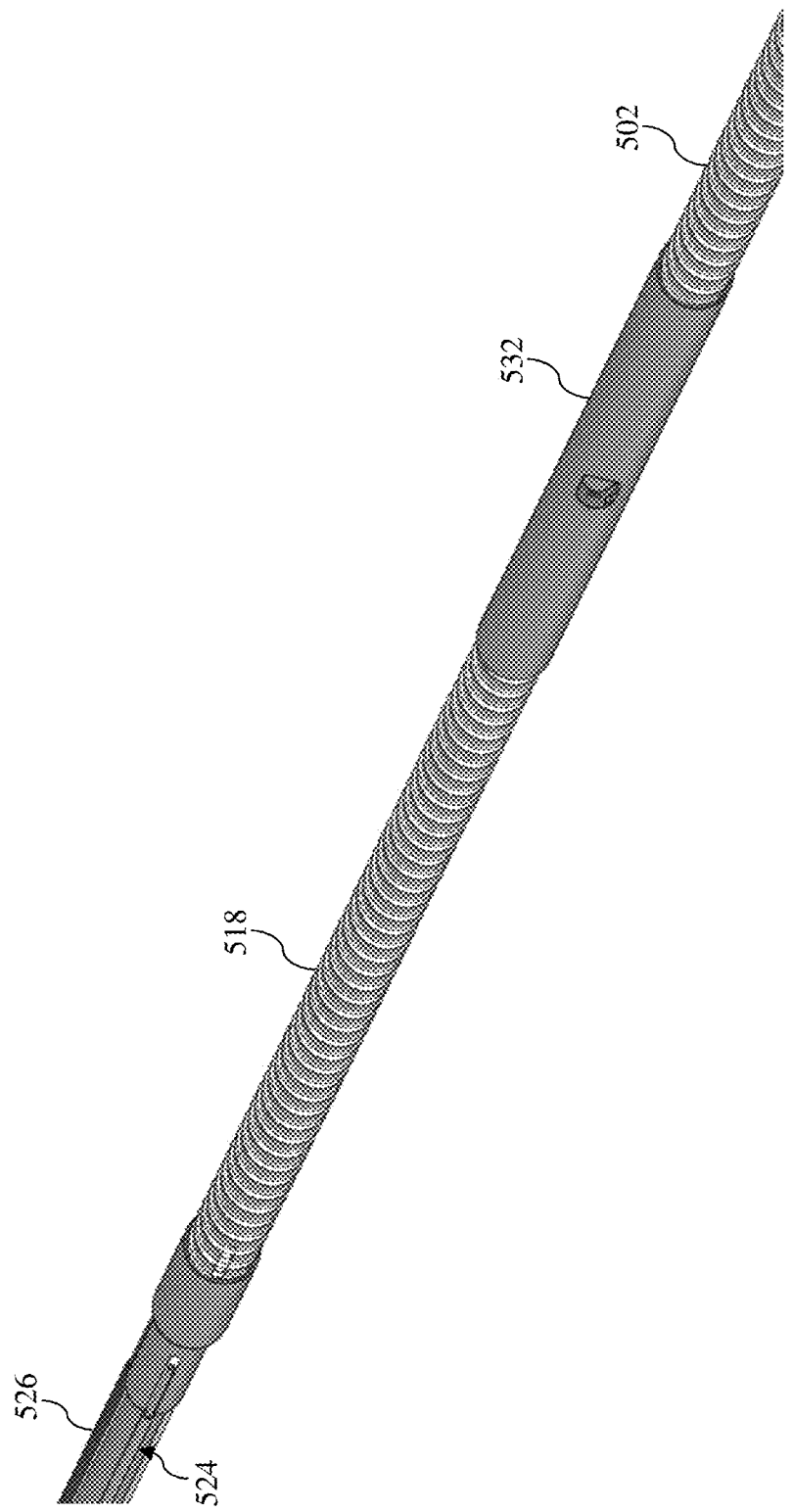
FIG. 29 is a diagrammatic perspective view of the proximal connector portion of FIGS. 26-28.

As shown in FIGS. 28 and 29, the electrical conductor 510 of the connector portion 500 is electrically coupled to a conductor 524 associated with another element 526 of an intravascular device, such as flexible elongate member 106 and/or a core wire of the flexible elongate member 106. In particular, the opening 522 in the tubular member provides access to the conductor 510 adjacent the distal end of the tubular member. Accordingly, the conductor 524 associated with element 526 can be electrically coupled to the conductor 510 using the opening 522. A similar approach can be utilized to connect the remaining conductors of the element

526 with the conductors of the tubular member of the connector portion 500, as described above in the context of FIG. 19 for example.

In some instances, the proximal connector portions of the present disclosure are configured to be manufactured as subassemblies. In that regard, at least the proximal connector portions 150 and 500 can be fully assembled and tested for electrical continuity as a separate component prior to being electrically and/or physically coupled to a flexible elongate member of the intravascular device. This helps to improve the overall manufacturing process of the intravascular device.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of assembling an intravascular device, comprising:
   exposing, at a proximal portion of a sensing guidewire, a section of a first conductor embedded within a sidewall of a tubular member of the guidewire, the sidewall comprising an insulating material, wherein the first conductor is coupled to a physiological sensor positioned at a distal portion of the guidewire, and wherein the exposing comprises removing the insulating material of the sidewall covering the section of the first conductor to expose the section of the first conductor;
   positioning a first conductive member around the tubular member adjacent to the exposed section of the first conductor; and
   electrically coupling the first conductive member to the first conductor such that the first conductive member is electrically coupled to the physiological sensor via the first conductor, wherein electrically coupling the first conductor to the first conductive member comprises filling a gap between the first conductor and the first conductive member with a flowable conductive material and solidifying the flowable conductive material to form an electrical connection between the first conductive member and the first conductor, wherein the gap is at least partially defined by a space created from the removing the insulating material of the sidewall covering the section of the first conductor.

2. The method of claim 1, further comprising:
   positioning a first insulating member around the tubular member adjacent to the first conductive member;
   positioning a second conductive member around the tubular member adjacent to the first insulating member such that the first insulating member is positioned between the first and second conductive members; and
   electrically coupling a second conductor embedded within the tubular member to the second conductive member.

3. The method of claim 2, further comprising exposing a section of the second conductor embedded within the tubular member, wherein the second conductive member is positioned around the tubular member adjacent to the exposed section of the second conductor.

4. The method of claim 1, wherein the exposed section of the first conductor has a longitudinal length greater than a longitudinal length of the first conductive member.

5. The method of claim 4, wherein the filling the gap comprises introducing the flowable conductive material into the gap via at least one of proximal opening or a distal opening resulting from the first conductor extending past at least the first conductive member.

6. The method of claim 1, further comprising exposing a portion of the first conductor embedded within tubular member adjacent to an end of the tubular member.

7. The method of claim 6, further comprising electrically coupling an electrical lead to the exposed portion of the first conductor.

8. The method of claim 7, wherein the physiological sensor is selected from the group of components consisting of an electronic component, an optical component, and an electro-optical component.

9. The method of claim 1, wherein the first conductor extends longitudinally within the sidewall of the tubular member, and wherein exposing the section of the first conductor comprises forming an elongated opening in a side of the sidewall, the elongated opening extending parallel to the exposed section of the first conductor.

10. An intravascular device, comprising:
    a sensing guidewire comprising a flexible elongate member comprising a proximal portion, a distal portion, and a physiological sensor positioned at the distal portion; and
    a proximal connector coupled to the proximal portion of the flexible elongate member, the proximal connector including:
       a tubular member comprising a sidewall formed of an insulating material and a plurality of conductors embedded within the sidewall and electrically coupled to the physiological sensor; and
       a first conductive member positioned around the tubular member and electrically coupled to a first conductor of the plurality of embedded conductors such that the first conductive member is electrically coupled to the physiological sensor via the first conductor, wherein the first conductive member is electrically coupled to the first conductor by a conductive material filling a gap between the first conductor and the first conductive member adjacent the sidewall of the tubular member covering the first conductor, and wherein the conductive material includes at least one of a soldering material or a conductive adhesive.

11. The intravascular device of claim 10, wherein the proximal connector further comprises:
    a first insulating member positioned around the tubular member adjacent to the first conductive member; and
    a second conductive member positioned around the tubular member adjacent to the first insulating member such that the first insulating member is positioned between the first and second conductive members, the second conductive member electrically coupled to a second conductor of the plurality of embedded conductors.

12. The intravascular device of claim 11, wherein the proximal connector further comprises:
    a second insulating member positioned around the tubular member adjacent to the second conductive member; and a third conductive member positioned around the tubular member adjacent to the second insulating member such that the second insulating member is positioned between the second and third conductive members, the third conductive member electrically coupled to a third conductors of the plurality of embedded conductors.

13. The intravascular device of claim 12, wherein the first, second, and third conductors are equally spaced about a circumference of the tubular member.

14. The intravascular device of claim 10, wherein each of the plurality of conductors extends longitudinally within the sidewall of the tubular member, and wherein the gap comprises an elongated opening in a side of the sidewall, the elongated opening extending parallel to the first conductor.

* * * * *